(12) United States Patent
Vo-Dinh et al.

(10) Patent No.: US 11,324,797 B2
(45) Date of Patent: *May 10, 2022

(54) PLASMONICS-ACTIVE METAL NANOSTAR COMPOSITIONS AND METHODS OF USE

(71) Applicant: Duke University, Durham, NC (US)

(72) Inventors: Tuan Vo-Dinh, Chapel Hill, NC (US); Hsiangkuo Yuan, Chalfont, PA (US); Andrew Fales, Durham, NC (US)

(73) Assignee: DUKE UNIVERSITY, Durham, NC (US)

(*) Notice: Subject to any disclaimer, the term of this patent is extended or adjusted under 35 U.S.C. 154(b) by 107 days.

This patent is subject to a terminal disclaimer.

(21) Appl. No.: 15/785,615

(22) Filed: Oct. 17, 2017

(65) Prior Publication Data

US 2018/0050077 A1 Feb. 22, 2018

Related U.S. Application Data

(62) Division of application No. 13/888,226, filed on May 6, 2013, now Pat. No. 9,789,154.

(60) Provisional application No. 61/642,728, filed on May 4, 2012.

(51) Int. Cl.

| A61K 38/02 | (2006.01) |
|---|---|
| A61K 49/00 | (2006.01) |
| A61K 41/00 | (2020.01) |
| A61K 47/62 | (2017.01) |
| A61K 47/69 | (2017.01) |

(52) U.S. Cl.
CPC .......... *A61K 38/02* (2013.01); *A61K 41/0066* (2013.01); *A61K 41/0071* (2013.01); *A61K 47/62* (2017.08); *A61K 47/6923* (2017.08); *A61K 49/0065* (2013.01)

(58) Field of Classification Search
None
See application file for complete search history.

(56) References Cited

U.S. PATENT DOCUMENTS

| 7,285,835 | B2 | 10/2007 | Rizzo et al. |
| 7,699,979 | B2 | 4/2010 | Li et al. |
| 7,951,535 | B2 | 5/2011 | Vo-Dinh |
| 8,045,152 | B2 | 10/2011 | Halas et al. |
| 2008/0266555 | A1 | 10/2008 | Murphy |
| 2009/0017480 | A1 | 1/2009 | Porter et al. |
| 2009/0137418 | A1 | 5/2009 | Miller et al. |
| 2009/0303461 | A1 | 12/2009 | Sun et al. |
| 2010/0025491 | A1 | 2/2010 | Finocchio |
| 2010/0254911 | A1 | 10/2010 | Sharma et al. |
| 2011/0052671 | A1 | 3/2011 | Zasadzinkski et al. |
| 2011/0269148 | A1 | 11/2011 | Huang et al. |

FOREIGN PATENT DOCUMENTS

| WO | 2007044057 A2 | 4/2007 |
| WO | 2010009106 A1 | 1/2010 |

OTHER PUBLICATIONS

Arosio et al. Cyclic RGD functionalized gold nanoparticles for tumor targeting. 2011 Bioconjug. Chem. 22: 664-672. Epub Mar. 24, 2011. (Year: 2011).*
Santos-Cuevas et al. Design, preparation, in vitro and in vivo evaluation of (99m)Tc-N2S2-Tat(49-57)-bombesin: a target-specific hybrid radiopharmaceutical. 2009 Int. J. Pharm. 375: 75-83. (Year: 2009).*
USPTO, Non-Final Rejection for U.S. Appl. No. 13/971,822, dated Jun. 15, 2016.
USPTO, Non-Final Rejection for U.S. Appl. No. 14/861,353, dated Sep. 1, 2016.
Wang and Vo-Dinh Multiplex detection of breast cancer biomarkers using plasmonic molecular sentinel nanoprobes Nanotechnology. Feb. 11, 2009; 20(6).
Buzdin et al., Stem-Loop Oligonucleotides as Hybridization Probes and Their Practical Use in Molecular Biology and Biomedicine. Ch 4, pp. 85-96., in book: Nucleic Acids Hybridization Modern Applications, 2007, Springer Press.
USPTO, Non-Final Rejection for U.S. Appl. No. 14/024,565, dated Jan. 20, 2016.
Schutz et al. Hydrophilically stabilized gold nanostars as SERS labels for tissue imaging of the tumor suppressor p63 by immuno-SERS microscopy. 2011 Chem. Commun. 47:4216-4218. Published online Feb. 28, 2011.
Alric et al. Gadolinium chelate coated gold nanoparticles as contrast agents for both X-ray computed tomography and magnetic resonance imaging. 2008 J. Am. Chem. Soc. 130: 5908-5915.
Jang et al. Gold nanorod-photosensitizer complex for near-infrared fluorescence imaging and photodynamic/photothermal therapy in vivo. 2011 ACS Nano 5: 1086-1094. Published online Jan. 18, 2011.
Zhang, L. W.; Monteiro-Riviere, N. A. Toxicol. Sci. 2009, 110, (1), 138-155.
Iversen, T.-G.; Skotland, T.; Sandvig, K. Nano Today 2011, 6, (2), 176-185.
Chen S, Wang ZL, Ballato J, Foulger SH, Carroll DL. J Am Chem Soc. Dec. 31, 2003;125(52):16186-7.
Hao F, Nehl CL, Hafner JH, Nordlander P. Nano Lett. Mar. 2007;7(3):729-32.

(Continued)

*Primary Examiner* — Jennifer Lamberski
(74) *Attorney, Agent, or Firm* — NK Patent Law

(57) ABSTRACT

Plasmonics-active metal nanostars are provided that can be used for treating and detecting cells in a subject. The modes of treatment include a photo-activated drug, which is activated by the photo-response of the nanostar to electromagnetic stimulation; a thermally-activated drug, which is activated by a thermal response of the nanostar to electromagnetic stimulation; and the thermal response of the nanostar itself to electromagnetic stimulation, which may directly or indirectly cause the death of an undesirable cell. Uptake of nanostars by undesirable cells may also aid in detection, by enhancing contrast or otherwise transforming electromagnetic stimulation during imaging.

12 Claims, 15 Drawing Sheets

Specification includes a Sequence Listing.

(56) References Cited

OTHER PUBLICATIONS

Senthil Kumar P, Pastoriza-Santos I, Rodriguez-Gonzalez B, Garcia De Abajo FJ, Liz-Marzan LM. Nanotechnology. 2008;19(1):015606-12.
Steel, A. B.; Herne, T. M.; Tarlov, M. J. Anal. Chem. 1998, 70, 4670-7.
Herne, T. M.; Tarlov, M. J. J. Am. Chem. Soc. 1997, 119, 8916-20.
Burges, J D.; Hawkridge, F. M. Langmuir 1997, 13, 3781-6.
Boncheva, M.; Scheibler, L.; Lincoln, P.; Vogel, H.; Akerman, B. Langmuir 1999, 15, 4317-20.
Kneipp, J.; Kneipp, H.; Rajadurai, A.; Redmond, R. W.; Kneipp, K. Optical probing and imaging of live cells using SERS labels. J. Raman Spectrosc. 2009, 40, (1), 1-5.
Potyrailo RA, Conrad RC, Ellington AD, Hieftje GM. Anal Chem. American Chemical Society; Aug. 1998;70(16):3419-25.
Hainfeld et al., The British Journal of Radiology, 79, 248, 2006.
James F Hainfeld, Daniel N Slatkin and Henry M Smilowitz, The use of gold nanoparticles to enhance radiotherapy in mice, Phys Med. Biol. 49, 2004.
Sang Hyun Cho, Estimation of tumour dose enhancement due to gold nanoparticles during typical radiation treatments: a preliminary Monte Carlo study, Phys. Med. Biol. 50, 2005.
Minelli, C.; Lowe, S. B.; Stevens, M. M., Engineering Nanocomposite Materials for Cancer Therapy, Small 2010, 6, (21), 2336-2357.
Janib, S. M.; Moses, A. S.; Mackay, J. A. Imaging and drug delivery using theranostic nanoparticles, Adv. Drug Deliver. Rev. 2010, 62, (11), 1052-1063.
Lammers, T.; Kiessling, F.; Hennink, W. E.; Storm, G., Nanotheranostics and Image-Guided Drug Delivery: Current Concepts and Future Directions, Mal. Pharm. 2010, 7, (6), 1899-1912.
Xie, J.; Lee, S.; Chen, X., Nanoparticle-based theranostic agents, Adv. Drug Deliver. Rev. 2010, 62, (11), 1064-1079.
Miura, S.; Couvreur, P., Nanotheranostics for personalized medicine, Adv Drug Deliv Rev 2012, 64, (13), 1394-416.
Vo-Dinh, T.; Hiromoto, M. Y. K.; Begun, G. M.; Moody, R. L., Surface-enhanced Raman spectrometry for trace organic analysis, Anal. Chem. 1984, 56, (9), 1667-1670.
Vo-Dinh, T.; Meier, M.; Wokaun, A., Surface-enhanced Raman spectrometry with silver particles on stochastic-post substrates, Anal. Chim. Acta. 1986, 181, (0), 139-148.
Vo-Dinh, T., Surface-enhanced Raman spectroscopy using metallic nanostructures. Trends Analyt. Chem, 1998, 17, (8-9), 557-582.
Vo-Dinh, T.; Dhawan, A.; Norton, S. J.; Khoury, C. G.; Wang, H.-N.; Misra, V.; Gerhold, M.D., Plasmonic Nanoparticles and Nanowires: Design, Fabrication and Application in Sensingt, J. Phys. Chem. C 2010, 114, (16), 7480-7488.
Fales, A. M.; Yuan, H.; Vo-Dinh, T. Silica-Coated Gold Nanostars for Combined Surface-Enhanced Raman Scattering (SERS) Detection and Singlet-Oxygen Generation: A Potential Nanoplatform for Theranostics. Langmuir 2011, 27, (19), 12186-12190.
Yuan, H.; Fales, A. M.; Vo-Dinh, T. TAT Peptide-Functionalized Gold Nanostars: Enhanced Intracellular Delivery and Efficient NIR Photothermal Therapy Using Ultralow Irradiance. J. Am. Chem. Soc. 2012, 134, (28), 11358-11361.
Yuan, H.; Khoury, C. G.; Wilson, C. M.; Grant, G. A.; Bennett, A. J.; Vo-Dinh, T. In vivo particle tracking and photothermal ablation using plasmon-resonant gold nanostars. Nanomedicine 2012, 8, (8), 1355-63.
Balint, S.; Rao, S.; Marro, M.; Miskovsky, P.; Petrov, D. Monitoring of local pH in photodynamic therapy-treated live cancer cells using surface-enhanced Raman scattering probes. J. Raman Spectrosc. 2011, 42, (6), 1215-1221.
Kircher, M. F.; De La Zerda, A.; Jokerst, J. V.; Zavaleta, C. L.; Kempen, P. J.; Mitira, E.; Pitter, K.; Huang, R.; Campos, C.; Habte, F.; Sinclair, R.; Brennan, C. W.; Mellinghoff, I. K.; Holland, E. C.; Gambhir, S. S. A brain tumor molecular imaging strategy using a new triple-modality MRI-photoacoustic-Raman nanoparticle. Nat Med 2012, 18, {5}, 829-834.
Alvarez-Puebla, R. A.; Liz-Marzan, L. M. SERS-Based Diagnosis and Biodetection. Small 2010, 6, (5), 604-610.
Kneipp, J.; Kneipp, H.; Witiig, B.; Kneipp, K. Following the Dynamics of pH in Endosomes of Live Cells with SERS Nanosensorst. J. Phys. Chem. C 2010, 114, (16), 7421-7426.
Qian, X. M.; Nie, S. M. Single-molecule and single-nanoparticle SERS: from fundamental mechanisms to biomedical applications. Chem. Soc. Rev. 2008, 37, (5), 912-920.
Faulds, K.; Smith, W. E.; Graham, D. Evaluation of Surface-Enhanced Resonance Raman Scattering for Ouantitative DNA Analysis. Anal. Chem. 2003, 76, (2), 412-417.
Rodriguez-Lorenzo, L.; Krpetic, Z.; Barbosa, S.; Alvarez-Puebla, R. A.; Liz-Marzan, L. M.; Prior, A.; Brust, M. Intracellular mapping with SERS-encoded gold nanostars. Integr. Biol. 2011, 3, (9), 922-926.
Kustner, B.; Gellner, M.; Schutz, M.; Schoppler, F.; Marx, A.; Strobel, P.; Adam, P.; Schmuck, C.; Schlocker, S. SERS Labels for Red Laser Excitation: Silica-Encapsulated SAMs on Tunable Gold/Silver Nanoshells. Angew. Chem. Int. Edit. 2009,48, {11 ), 1950-1953.
Cao, Y. C.; Jin, R.; Nam, J.-M.; Thaxton, C. S.; Mirkin, C. A. Raman Dye-Labeled Nanoparticle Probes for Proteins. J. Am. Chem. Soc. 2003,125, (48), 14676-14677.
Wang, G.; Park, H.-Y.; Lipert, R. J.; Porter, M. D. Mixed Monolayers on Gold Nanoparticle Labels for Multiplexed Surface-Enhanced Raman Scattering Based Immunoassays. Anal. Chem. 2009, 81, (23), 9643-9650.
Gregas, M. K.; Yan, F.; Scaffidi, J.; Wang, H.-N.; Vo-Dinh, T. Characterization of nanoprobe uptake in single cells: spatial and temporal tracking via SERS labeling and modulation of surface charge. Nanomedicine: NBM 2011, 7, (1), 115-122.
Gregas, M. K.; Scaffidi, J. P.; Lauly, B.; Vo-Dinh, T. Surface-Enhanced Raman Scattering Detection and Fracking of Nanoprobes: Enhanced Uptake and Nuclear Targeting in Single Cells. Appl. Spectrosc. 2010, 64, (8), 858-866.
Zavaleta, C. L.; Smith, B. R.; Walton, I.; Doering, W.; Davis, G.; Shojaei, B.; Natan, M. J.; Gambhir, S. S. Multiplexed imaging of surface enhanced Raman scattering nanotags in living mice using noninvasive Raman spectroscopy. Proc. Natl. Acad. Sci. U S A 2009, 106, {32}, 13511-13516.
Keren, S.; Zavaleta, C.; Cheng, Z.; De Lazerda, A.; Gheysens, O.; Gambhir, S. S. Noninvasive molecular imaging of small living subjects using Raman spectroscopy. Proc. Natl. Acad. Sci. U S A 2008, 105, (15), 5844-5849.
Kim, J.-H.; Kim, J.-S.; Choi, H.; Lee, S.-M.; Jun, B.-H.; Yu, K.-N.; Kuk, E.; Kim, Y.-K.; Jeong, D. H.; Cho, M.-H.; Lee, Y.-S. Nanoparticle Probes with Surface Enhanced Raman Spectroscopic Tags for Cellular Cancer Targeting. Anal. Chem. 2006, 78, (19), 6967-6973.
Lam, M.; Oleinick, N. L.; Nieminen, A.-L. Photodynamic Therapy-induced Apoptosis in Epidermoid Carcinoma Dells. J. Biol. Chem. 2001, 276, (50), 47379-47386.
Durr, N.J.; Weisspfennig, C.T.; Holfeld, B.A.; Ben-Yakar, A.J. Biomed. Opt 2011, 16, (2), 026008.
Pan, L; He, Q.; Liu, J.; Chen, Y.; Ma, M.; Zhang, L.; Shi, J.J. Am. Chem. Soc. 2012, 120320133341008.
Pante, N.; Kann, M. Moi. Biol. Cell 2002, 13, (2), 425-434.
Mishra, A; Lai, G.H.; Schmidt, N.W.; Sun, V.Z.; Rodriguez, A.R.; Tong, R.; Tang, L.; Cheng, J.; Deming, T.J.; Kamei, D.T.; Wong, G.C.L. Proc Natl. Acad. Sci. U.S.A. 2011,108, (41), 16883-16888.
Hrelescu et al. Single gold nanostars enhance Raman scattering. 2009 Appl. Phys. Lett. 94: 153113, 3 pages.
Dondapati et al. Label-free biosensing based on single gold nanostars as plasmonic transducers. 2010. ACSNano 4: 6318- 6322.
Ohulchanskyy, T. Y.; Roy, I.; Goswami, L. N.; Chen, Y.; Bergey, E. J.; Pandey, R. K.; Oseroff, A. R.; Prasad, P. N. Organically Modified Silica Nanoparticles with Covalently Incorporated Photosensitizer for Photodynamic Therapy of Cancer. Nano Lett. 2007, 7, (9), 2835-2842.
Kim, S.; Ohulchanskyy, T. Y.; Pudavar, H. E.; Pandey, R. K.; Prasad, P. N. Organically Modified Silica Nanoparticles Co-encapsulating Photosensitizing Drug and Aggregation-Enhanced Two-Photon Absorbing Fluorescen Dye Aggregates for Two-Photon Photodynamic Therapy. J. Am. Chem. Soc. 2007, 129, (9), 2669-2675.
Yan, F.; Kopelman, R. The Embedding of Meta-tetra(Hydroxyphenyl)-Chlorin into Silica Nanoparticle Platforms for Photodynamic Therapy

(56) References Cited

OTHER PUBLICATIONS and Their Singlet Oxygen Production and pH-dependent Optical Properties. Photochem. Photobiol. 2003, 78, (6), 587-591.
Lu, J.; Liong, M.; Zink, J. I.; Tamanoi, F. Mesoporous Silica Nanoparticles as a Delivery System for Hydrophobic Anticancer Drugs. Small 2007, 3, (8), 1341-1346.
Yuan, H.; Fales, A. M.; Khoury, C. G.; Liu, J.; Vo-Dinh, T., J. Raman Spectrosc. 2012.
Fernandez-Lopez, C.; Mateo-Mateo, C.; Alvarez-Puebla, R. N. A.; Perez-Juste, J.; Pastoriza-Santos, I.; Liz-Marzan, L. M. Highly Controlled Silica Coating of PEG-Capped Metal Nanoparticles and Preparation of SERS-Encoded Particlest Langmuir 2009, 25, (24), 13894-13899.
Rodriguez-Lorenzo, Plasmonic nanosensors with inverse sensitivity by means of enzyme-guided crystal growth, May 27, 2012.
Kneipp, J.; Kneipp, H.; Rice, W. L.; Kneipp, K. Optical Probes for Biological Applications Based on Surface-Enhanced Raman Scattering from Indocyanine Green on Gold Nanoparticles. Anal. Chem. 2005, 77, (8), 2381-2385.
ISA/KR; International Search Report and Written Opinion for International Application No. PCT/US2013/059312, dated Dec. 5, 2013.
USPTO; Non-Final Office Action for U.S. Appl. No. 13/888,226 dated Jan. 12, 2017.
USPTO; Non-Final Office Action for U.S. Appl. No. 13/888,226 dated Jan. 11, 2016.
USPTO; Final Office Action for U.S. Appl. No. 13/888,226 dated Jun. 28, 2016.
USPTO; Non-Final Office Action for U.S. Appl. No. 15/408,563 dated Sep. 8, 2017.
USPTO; Final Office Action for U.S. Appl. No. 14/024,565 dated Oct. 26, 2016.
USPTO; Non-Final Office Action for U.S. Appl. No. 15/442,731 dated Jul. 28, 2017.
USPTO; Final Office Action for U.S. Appl. No. 15/442,731 dated Sep. 18, 2018.
USPTO; Final Office Action for U.S. Appl. No. 15/442,731 dated Jun. 15, 2018.
USPTO; Non-Final Office Action for U.S. Appl. No. 14/861,353 dated Dec. 21, 2017.
USPTO; Final Office Action for U.S. Appl. No. 14/861,353 dated Jul. 24, 2018.
USPTO; Final Office Action for U.S. Appl. No. 14/861,353 dated Apr. 18, 2017.
USPTO; Restriction Requirement for U.S. Appl. No. 13/888,226 dated Nov. 5, 2015.
USPTO; Restriction Requirement for U.S. Appl. No. 13/971,822 dated Jan. 25, 2016.
USPTO; Restriction Requirement for U.S. Appl. No. 14/024,565 dated Aug. 25, 2015.
USPTO; Restriction Requirement for U.S. Appl. No. 14/861,353 dated Apr. 21, 2016.
"List of sequences bacterial genomes", (Wikipedia.com; accessed Jan. 24, 2014).
"Viruses" (Wikipedia.com; accessed Nov. 24, 2012).
"How many species of bacteria are there" (wisegeek.com; accessed Jan. 21, 2014).
"Fungi", (Wikipedia.com; accessed Jun. 3, 2013).
"Plant", (Wikipedia.com; accessed Aug. 28, 2015).
"Mammal", (Wikipedia.com; accessed Sep. 22, 2011).
"Murinae", (Wikipedia.com; accessed Mar. 18, 2013).
"Fish", (Wikipedia.com; accessed Nov. 2, 2014).
Tang, W.; Xu, H.; Kopelman, R.; Philbert, M. A. Photodynamic Characterization and In Vitro Application of Methylene Blue-containing Nanoparticle Platforms. Photochem. Photobiol. 2005, 81, (2), 242-249.
Rossi, L. M.; Silva, P. R.; Vono, L. L. R.; Fernandes, A. U.; Tada, D. B.; Baptista, M. C. S. Protoporphyrin IX Nanoparticle Carrier: Preparation, Optical Properties, and Singlet Oxygen Generation. Langmuir 2008, 24, (21), 12534-12538.
Lee, S. J.; Koo, H.; Lee, D. E.; Min, S.; Lee, S.; Chen, X.; Choi, Y.; Leary, J. F.; Park, K.; Jeong, S. Y.; Kwon, I. C.; Kim, K.; Choi, K. Tumor-homing photosensitizer-conjugated glycol chitosan nanoparticles for synchronous photodynamic imaging and therapy based on cellular on/off system. Biomaterials 2011, 32, (16), 4021-4029.
Bechet, D.; Couleaud, P.; Frochot, C.; Viriot, M.-L.; Guillemin, F.; Barberi-Heyob, M. Nanoparticles as vehicles for delivery of photodynamic therapy agents. Trends Biotechnol. 2008, 26, (11), 612-621.
Roy, I.; Ohulchanskyy, T. Y.; Pudavar, H. E.; Bergey, E. J.; Oseroff, A. R.; Morgan, J.; Dougherty, T. J.; Prasad, P. N. Ceramic-Based Nanoparticles Entrapping Water-Insoluble Photosensitizing Anticancer Drugs: A Novel Drug-Carrier System for Photodynamic Therapy. J. Am. Chem. Soc. 2003, 125, (26), 7860-7865.
WIPO; International Search Report dated Dec. 5, 2013 for application PCT/US2013/059312 filed Sep. 11, 2013.
Kievit, F. M.; Zhang, M. Adv. Mater. (Weinheim, Ger.) 2011, 23, (36), H217-47.
Shi, J.; Votruba, A. R.; Farokhzad, 0. C.; Langer, R. Nano Lett. 2010, 10, (9), 3223-3230.
Farrell, D.; Alper, J.; Ptak, K.; Panaro, N. J.; Grodzinski, P.; Barker, A. D. ACS Nano 2010, 4, (2), 589-594.
Chadwick, S.; Kriegel, C.; Amiji, M. Adv. Drug Delivery Rev. 2010, 62, (4-5), 394-407.
Riehemann, K.; Schneider, S. W.; Luger, T. A.; Godin, B.; Ferrari, M.; Fuchs, H. Angew. Chem., Int. Ed. Engl. 2009, 18, (5), 872-897.
Wang, X.; Yang, L.; Chen, Z. G.; Shin, D. M. CA Cancer J Clin 2008, 58, (2), 97-110.
Nie, S.; Xing, Y.; Kim, G. J.; Simons, J. W. Annu. Rev. Biomed. Eng. 2007, 9, 257-288.
Hahn, M. A.; Singh, A. K.; Sharma, P.; Brown, S. C.; Moudgil, B. M. Anal. Bioanal. Chem. 2011, 399, (1), 3-27.
Ghosh, P.; Han, G.; De, M.; Kim, C. K.; Rotello, V. M. Adv. Drug Delivery Rev. 2008, 60, (11), 1307-1315.
Huang, L.; Liu, Y. Annu. Rev. Biomed. Eng. 2011, 13, (1), 507-530.
Juzenas, P.; Chen, W.; Sun, Y.-P.; Neto Coelho, M. A.; Generalov, R.; Generalova, N.; Christensen, I. L. Adv. Drug Delivery Rev. 2008, 60, (15), 1600-1614.
Kennedy, L. C.; Bickford, L. R.; Lewinski, N. A.; Coughlin, A. J.; Hu, Y.; Day, E. S.; West, J. L.; Drezek, R. A. Small 2011, 7, (2), 169-183.
Ruoslahti, E.; Bhatia, S. N.; Sailor, M. J. J. Cell Biol. 2010, 188, (6), 759-768.
Peer, D.; Karp, J. M.; Hong, S.; Farokhzad, 0. C.; Margalit, R.; Langer, R. Nat. Nanotechnol. 2007, 2, (12), 751-760.
Hu, M.; Chen, J.; Li, Z.-Y.; Au, L.; Hartland, G. V.; Li, X.; Marquez, M.; Xia, Y. Chem. Soc. Rev. 2006, 35, (11), 1084-1094.
Boisselier, E.; Astruc, D. Chem. Soc. Rev. 2009, 38, (6), 1759-1782.
Weissleder, R. Nat. Biotechnol. 2001, 19, (4), 316-317.
Guerrero-Martinez, A.; Barbosa, S.; Pastoriza-Santos, L; Liz-Marzan, L. M. Curr. Opin. Colloid Interface Sci. 2011, 16, (2), 118-127.
Yuan, H.; Khoury, C. G.; (Co-First Author); Hwang, H.; Wilson, C. M.; Grant, G. A.; Vo-Dinh, T. Nanotechnology 2012, 23, (7), 075102.
Austin, L. A.; Kang, B.; Yen, C.-W.; El-Sayed, M. A. J. Am. Chem. Soc. 2011, 133, (44), 17594-17597.
Tkachenko, A. G.; Xie, H.; Liu, Y.; Coleman, D.; Ryan, J.; Glomm, W. R.; Shipton, M. K.; Franzen, S.; Feldheim, D. L. Bioconjugate Chem. 2004, 15, (3), 482-490.
Tong, L.; Wei, O.; Wei, A.; Cheng, J.-X. Photochem. Photobiol. 2009, 85, (1), 21-32.
Hutter, E.; Maysinger, D. Microsc. Res. Tech. 2010, 74, (7), 592-604.
Van De Broek, B.; Devoogdt, N.; D'Hollander, A.; Gijs, H.-L.; Jans, K.; Lagae, L.; Muyldermans, S.; Maes, G.; Borghs, G. ACS Nano 2011, 5, (6), 4319-4328.
Ansi, American National Standard for safe use of lasers. Laser Institute of America: Orlando, FL, 2000.
Huang, X.; Kang, B.; Qian, W.; Mackey, M. A.; Chen, P. C.; Oyelere, A. K.; El-Sayed, I. H.; El-Sayed, M. A. J. Biomed. Opt. 2010, 15, (5), 058002.

(56) References Cited

OTHER PUBLICATIONS

Au, L.; Zheng, D.; Zhou, F.; Li, Z.-Y.; Li, X.; Xia, Y. ACS Nano 2008, 2, (8), 1645-1652.
Kim, J.; Park, S.; Lee, J. E.; Jin, S. M.; Lee, J. H.; Lee, I. S.; Yang, I.; Kim, J.-S.; Kim, S. K.; Cho, M.-H.; Hyeon, T. Angew. Chem., Int. Ed. Engl. 2006, 45, (46), 7754-7758.
Patel, L.; Zaro, J.; Shen, W.-C. Pharm. Res. 2007, 24, 1977-1992.
Khalil, I. A.; Kogure, K.; Akita, H.; Harashima, H. Pharmacol. Rev. 2006, 58, (1), 32-45.
Levy, R.; Shaheen, U.; Cesbron, Y. Nano Rev. 2010, 1, 4889.
Lundqvist, M.; Stigler, J.; Elia, G.; Lynch, I.; Cedervall, T.; Dawson, K. A. Proc. Natl. Acad. Sci. U. S. A. 2008, 105, (38), 14265-14270.
Bartczak, D.; Muskens, 0. L.; Nitti, S.; Sanchez-Elsner, T.; Millar, T. M.; Kanaras, A. G. Small 2011.
Torchilin, V. P. Adv. Drug Delivery Rev. 2008, 60, (4-5), 548-558.
Wei, Y.; Jana, N. R.; Tan, S. J.; Ying, J. Y. Bioconjugate Chem. 2009, 20, {9}, 1752-1758.
Zhao, M.; Kircher, M. F.; Josephson, L.; Weissleder, R. Bioconjugate Chem. 2002, 13, (4), 840-844.
Rao, K. S.; Reddy, M. K.; Horning, J. L.; Labhasetwar, V. Biomaterials 2008, 29, {33}, 4429-4438.
Tian, X.-H.; Wei, F.; Wang, T.-X.; Wang, D.; Wang, J.; Lin, X.-N.; Wang, P.; Ren, L. Mater. Lett. 2012, 68, 94-96.
Wadia, J. S.; Stan, R. V.; Dowdy, S. F. Nat. Med. 2004, 10, (3), 310-315.
Ruan, G.; Agrawal, A.; Marcus, A. I.; Nie, S. J. Am. Chem. Soc. 2007, 129, (47), 14759-14766.
Pallaoro, A.; Braun, G. B.; Moskovits, M. Proc. Natl. Acad. Sci. U. S. A. 2011, 108, (40), 16559-16564.
Lewin, M.; Carlesso, N.; Tung, C. H.; Tang, X. W.; Cory, D.; Scadden, D. T.; Weissleder, R. Nat. Biotechnol. 2000, 18, (4), 410-414.
Krpetic, Z.; Saleemi, S.; Prior, I.A.; See, V.; Qureshi, R.; Brust, M. ACS Nano 2011, 5, (6), 5195-5201.
Berry, C.C.; De La Fuente, J.M.; Mullin, M.; Chu, S.W.L.; Curtis, A.S.G. IEEE Trans. Nanobioscience 2007, 6, (4), 262-269.
USPTO; Non-Final Office Action for U.S. Appl. No. 14/861,353 dated May 30, 2019, 18 pages.

\* cited by examiner

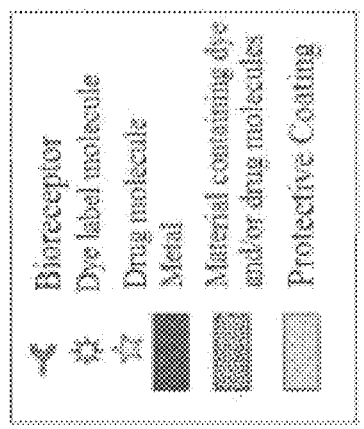
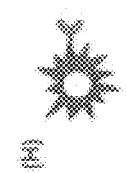
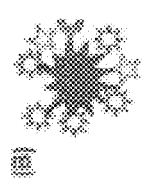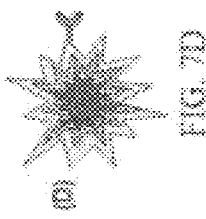
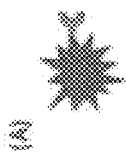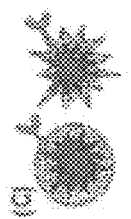
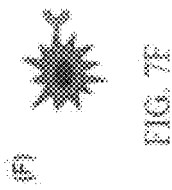
FIG. 7A FIG. 7B FIG. 7C FIG. 7D FIG. 7E FIG. 7F FIG. 7G FIG. 7H FIG. 7I

US 11,324,797 B2

SEQUENCE LISTING

<160> NUMBER OF SEQ ID NOS: 1

<210> SEQ ID NO 1
<211> LENGTH: 9
<212> TYPE: PRT
<213> ORGANISM: Artificial
<220> FEATURE:
<223> OTHER INFORMATION: Synthetic peptide

<400> SEQUENCE: 1

Arg Lys Lys Arg Arg Arg Asn Arg Cys
1               5

PLASMONICS-ACTIVE METAL NANOSTAR COMPOSITIONS AND METHODS OF USE

CROSS REFERENCE TO RELATED APPLICATIONS

This application is a divisional of U.S. patent application Ser. No. 13/888,226, filed on May 6, 2013 and entitled "PLASMONICS-ACTIVE METAL NANOSTAR COMPOSITIONS AND METHODS OF USE", which claims the benefit of U.S. Provisional Patent Application No. 61/642,728 filed on May 4, 2012 and entitled "MULTIPHOTON MULTIMODALITY THERAPY AND DIAGNOSTICS", the disclosures of which are incorporated herein by reference in their entireties.

TECHNICAL FIELD

The present disclosure relates to metal nanostars. Particularly, the present disclosure relates to methods for making and using plasmonics-active metal nanostars to treat and detect cells in vivo and ex vivo.

BACKGROUND

Nanoparticle systems have gained wide attention due to their potential in medicine, such as molecular imaging, immunization, theranostics, and targeted delivery/therapy.[1-7] Nanoparticles can be fabricated as strong contrast agents for different imaging modalities with superior signal-to-noise ratios than conventional agents.[8] or as therapeutic agents such as drug carriers,[9-10] radioenhancers,[11] and photothermal transducers.[12] Gold nanoparticles (AuNPs), with their facile synthesis and biocompatibility, have therefore been applied for a variety of therapeutics, especially in cancer therapy.[15, 16]

Gold nanostars (NS), with a high absorption-to-scattering ratio in the NIR, efficiently transduce photon energy into heat for hyperthermia therapy.[20,25] To date, most photermolysis studies utilize laser irradiation higher than the maximal permissible exposure (MPE) of skin by ANSI regulation.[26] To make photothermolysis applicable to real practice, one needs to enhance the photothermal transduction efficiency. One way is to use a pulsed laser instead of a continuous-wave laser, permitting efficient photothermal conversion by allowing additional time for electron-phonon relaxation.[12, 23, 27] Previously, in vitro photothermolysis using NIR pulsed laser reported irradiances of 1.6-48.6 $W/cm^2$;[23, 28, 29] which were higher than the MPE of skin (e.g. 0.4 $W/cm^2$ at 800 nm). Insufficient intracellular particle delivery and low photothermal transduction efficiency may be the main obstacles. Therefore, there is a strong need to design a more efficient photothermal transducer with optimized cellular uptake.

Recently, star-shaped AuNPs ("nanostars") have attracted interest because their plasmon can be tuned to the NIR region, and the structure contains multiple sharp tips that can greatly enhance incident electromagnetic fields. Studies have shown that NIR-absorbing nanorods, nanocages or nanoshells can be used as contrast agents in optical imaging techniques such as optical coherent tomography, two-photon luminescence (TPL) microscopy, and photoacoustic imaging. Their large absorption cross-sections can also effectively convert photon energy to heat during photothermal therapy. Nanostars, which absorb in the NIR, have been hypothesized to behave similarly. Nanostar-related bioapplications remain scarce in spite of their potential, mostly due to the difficulty of surface functionalization.

In 2003, Chen et al.[53] first reported the synthesis of multipod gold nanoparticles from silver plates in the presence of cetyltrimethylammonium bromide (CTAB) and NaOH. Later, several seedless or seed-mediated synthesis methods were employed using majorly poly(N-vinylpyrolidone) (PVP) or CTAB as surfactant. Further use of nanostars has been limited by (1) the potential toxicity of CTAB, (2) the difficulty of replacing PVP or CTAB during biofunctionalization, and (3) induction of aggregation following multiple washes. Previous experimental studies have shown a red-shifting of the plasmon peak from nanostars with longer or sharper branches. Several numerical studies of their plasmonic properties have recently been reported. Hao et al.'s[54] 2-D modeling of a single nanostar, consisting of 5 unique branches, with finite difference time domain (FDTD) method showed that nanostars plasmon results from the hybridization of plasmon resonance of each branch; the plasmon peak relative intensity depends on the polarization angle. Senthil et al.[55] also stated that the tip angle and radius, but not the number of branches, are the major determining factors in plasmon shift in a simplistic 2-branch model.

To achieve successful and selective photothermolysis or phototherapy, nanostars need to be delivered to the designated target cells without compromising cell viability. This requires overcoming several biological barriers. For example, particles need to be physiologically stable (i.e. non-aggregated, long serum half-life), bind to the cell surface, and traverse the plasma membrane.[30, 31] In general, nanoparticle size, shape, surface charge, and coating (e.g. protein corona, polymer, anti-fouling layer) all affect their cellular delivery.[32-34] People have tried numerous methods to increase the uptake of nanoparticles. One way to do this is achieved by surface coating with cell penetrating peptides (CPPs).[30]

CPPs, with 30 or less amino acids that are cationic or amphipathic in nature, facilitate the translocation across the cellular membrane. Human immunodeficiency virus type 1 (HIV-1) encoded Trans-Activator of Transcription (TAT) peptide, which is one of the most studied CPPs, has been employed to facilitate not only the intracellular delivery of various nanoparticles,[35-37] but also the crossing of the blood-brain barrier.[38, 39] It has been shown that TAT-labeled proteins and quantum dots (QD) enter cells by lipid raft mediated macropinocytosis,[40, 41] which is a particularly enticing uptake pathway in drug delivery because of the large uptake volume, avoidance of lysosomal degradation, and the ease of escaping from macropinosomes due to their inherent leakiness.[31] To date, although an enhanced cellular uptake of TAT-labeled gold nanoparticles (TAT-AuNPs) has already been observed,[32, 35, 42-46] the cellular uptake mechanism for TAT-AuNP remains unreported.

SUMMARY OF THE INVENTION

In general, one object of the present disclosure described herein comprises, consists of, or consists essentially of a method of treating undesirable cells in a subject comprising: administering to the subject nanostar particles and a photoactivated drug; and irradiating the nanostar whereby the nanostar emits a photo-response which activates the photoactivated drug.

One embodiment of the present disclosure is a plasmonics-active gold nanostar resulting from a process comprising, consisting of, or consisting essentially of: adding citrate stabilized gold seeds to a solution of tetrachloroauric acid (HAuCl$_4$) under acidic conditions; and mixing a silver salt compound and a weak reducing agent simultaneously into the solution of HAuCl$_4$ under conditions such that the plasmonics-active gold nanostars are produced.

One embodiment of the present disclosure is a method for preparing plasmonics-active gold nanostars, the method comprising, consisting of, or consisting essentially of: adding citrate stabilized gold seeds to a solution of tetrachloroauric acid (HAuCl$_4$) under acidic conditions; and mixing a silver salt compound and a weak reducing agent simultaneously into the solution of HAuCl$_4$ under conditions such that the plasmonics-active gold nanostars are produced.

One embodiment of the present disclosure is a method of treating undesirable cells in a subject comprising, consisting of, or consisting essentially of: administering to a subject a plasmonics-active gold or silver nanostar comprising: a bioreceptor, wherein the bioreceptor targets the nanostar to an undesirable cell; and one or more of a photosensitizer and a photoactivator, wherein the photosensitizer and the photoactivator absorb electromagnetic radiation emitted by the gold nanostar when the nanostar is excited by a single-photon or multi-photon excitation; and applying the single photon or multi-photon excitation to the subject such that the nanostar is excited and emits electromagnetic radiation that is absorbed by the photosensitizer and the photoactivator such that the undesirable cell is damaged by one or a combination of thermal energy emitted by the nanostar, reactive oxygen species (ROS) generated by the photosensiter, and one or a combination of activation and release of the photoactivator.

One embodiment of the present disclosure is an ex vivo method of treating undesirable cells comprising, consisting of, or consisting essentially of: contacting ex vivo a group of cells comprising an undesirable cell with a plasmonics-active gold or silver nanostar including: a bioreceptor, wherein the bioreceptor targets the nanostar to the undesirable cell; and one or more of a photosensitizer and a photoactivator, wherein the photosensitizer and the photoactivator absorb electromagnetic radiation emitted by the gold nanostar when the nanostar is excited by a single photon or multi-photon excitation; and applying the single-photon or multi-photon excitation to the group of cells such that the nanostar is excited and emits electromagnetic radiation that is absorbed by the photosensitizer and the photoactivator such that the undesirable cell is damaged by one or a combination of thermal energy emitted by the nanostar, reactive oxygen species (ROS) generated by the photosensiter, and one or a combination of activation and release of the photoactivator.

One embodiment of the present disclosure is a method of treating undesirable cells in a subject comprising, consisting of, or consisting essentially of: administering to a subject a plasmonics-active gold or silver nanostar comprising a bioreceptor, wherein the bioreceptor targets the nanostar to an undesirable cell; and applying a single-photon or multi-photon excitation to the subject such that the nanostar is excited and the undesirable cell is damaged by thermal energy emitted as a result of excitation of the nanostar.

One embodiment of the present disclosure is an ex vivo method of treating undesirable cells comprising, consisting of, or consisting essentially of: contacting ex vivo a group of cells comprising an undesirable cell with a plasmonics-active gold or silver nanostar comprising a bioreceptor, wherein the bioreceptor targets the nanostar to the undesirable cell; and applying a single-photon or multi-photon excitation to the group of cells such that the nanostar is excited and the undesirable cell is damaged by thermal energy emitted as a result of excitation of the nanostar.

One embodiment of the present disclosure is a method of treating undesirable cells in a subject comprising, consisting of, or consisting essentially of: administering to a subject a plasmonics-active gold or silver nanostar comprising: one or more of a photosensitizer and a photoactivator, wherein the photosensitizer and the photoactivator absorb electromagnetic radiation emitted by the nanostar when the nanostar is excited by a single-photon or multi-photon excitation; and applying the single photon or multi-photon excitation to the subject such that the nanostar is excited and emits electromagnetic radiation that is absorbed by the photosensitizer and the photoactivator such that the undesirable cell is damaged by one or a combination of thermal energy emitted by the nanostar, reactive oxygen species (ROS) generated by the photosensiter, and one or a combination of activation and release of the photoactivator.

Another aspect of the present disclosure comprises, consists of, or consists essentially of all that is disclosed and illustrated herein.

BRIEF DESCRIPTION OF THE DRAWINGS

The foregoing summary, as well as the following detailed description of various embodiments, is better understood when read in conjunction with the appended figures. For the purposes of illustration, there is shown in the Figures exemplary embodiments; however, the presently disclosed subject matter is not limited to the specific methods and exemplary embodiments disclosed.

FIG. 7A-7I are schematic diagrams showing a series of plasmonics-active nanostars with bioreceptor according to one or more embodiments of the present disclosure. 7A-7H show the plasmonics-active nanostars and 7I shows the legend.

DETAILED DESCRIPTION OF THE INVENTION

Figure 1:
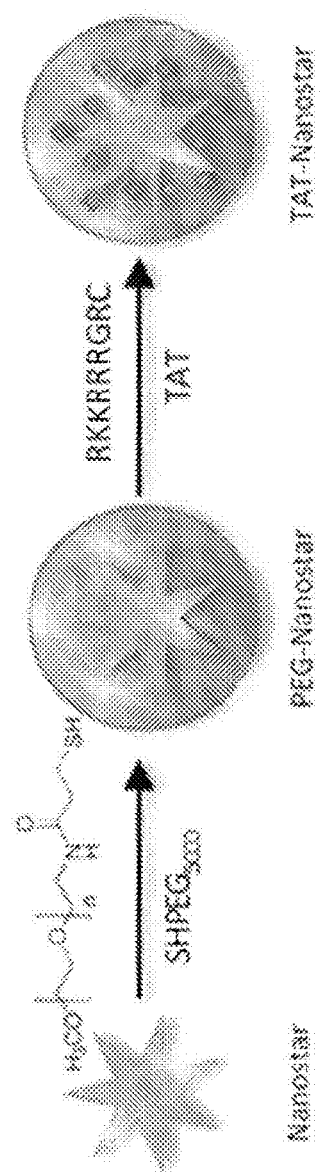
FIG. 1 is a diagram of a synthetic scheme for functionalization of gold nanostar (NS) with Human Immunodeficiency Virus (HIV) Trans-Activator of Transcription (TAT) peptide according to one or more embodiments of the present disclosure. Bare NS was coated with thiolated-PEG to stabilize the NS then with cysteine-terminated TAT.

For the purposes of promoting an understanding of the principles of the present disclosure, reference will now be made to preferred embodiments and specific language will be used to describe the same. It will nevertheless be understood that no limitation of the scope of the disclosure is thereby intended, such alteration and further modifications of the disclosure as illustrated herein, being contemplated as would normally occur to one skilled in the art to which the disclosure relates.

Articles "a" and "an" are used herein to refer to one or to more than one (i.e. at least one) of the grammatical object of the article. By way of example, "a cell" means at least one cell and can include a number of cells.

Unless otherwise defined, all technical terms used herein have the same meaning as commonly understood by one of ordinary skill in the art to which this disclosure belongs.

As used herein, the term "nanostar" or "NS" means a nanoparticle which has a single core section with two or more protrusions emitting from the core section of the nanoparticle. These protrusions are usually conical or pyramidal in form, but not always.

Gold nanostars (NS), which feature tunable plasmon bands in the near-infrared (NIR) tissue optical window,[17] bring forth potential for in vivo imaging and therapeutic applications.[18-20] Previously, metal nanoparticle imaging has required the use of fluorescent labels, which are generally quenched on the gold surface. Other non-fluorescent optical tracking methods, using dark-field or differential interference contrast, are typically inoperable in tissue samples.[21, 22] Gold NS, with their unique plasmon resonating with the NIR incident light, creates a non-linear field enhancement that yields intense two-photon photoluminescence (TPL). Their extremely high two-photon action cross section (e.g. $10^6$ GM), which is several orders of magnitude higher than that of organic fluorophores, allows both in vitro and in vivo real-time NS tracking without the use of fluorescence.[19, 20, 23, 24] The ability to visualize NS with high temporal and spatial resolution under multiphoton microscopy provides a tremendous flexibility in understanding nanoparticle kinetics/trafficking behavior in biomedical settings.

Thus, metal nanostars can be used to accomplish multiple therapeutic and detection goals simulataneously. As examples, metal nanostars can thermally activate or photoactivate drugs, they can thermally cause cell damage or death, and they can aid in detection and imaging; and drugs can be administered separately or together or bound to the nanostars or a matrix around the nanostars. In addition, functionalization of metal nanostars with bioreceptors can allow for targeting of the nanostars to specific cells and for enhanced intracellular delivery. In one embodiment of the present disclosure, a metal nanostar is provided that is functionalized with a cell penetrating peptide that can therefore bring forth enhanced intracellular delivery, which in turns allows efficient photothermolysis with lower irradiance. In one embodiment of the present disclosure, a TAT peptide-functionalized gold NS is provided for both enhanced intracellular delivery and efficient in vitro photothermolysis under an irradiance of 0.2 W/cm$^2$, which is lower than the MPE of skin.

In one embodiment, the present disclosure provides the development and synthesis of nanostar platforms. In one aspect, the present disclosure provides gold nanostars having unique properties for both therapy and diagnostics. A simple synthesis is provided for gold nanostars without a chemical or polymer coating. Star-shaped AuNPs ("nanostars") have attracted interest because their plasmon can be tuned to the NIR region, and the structure contains multiple sharp tips that can greatly enhance incident electromagnetic fields. Studies have shown that NIR-absorbing nanorods, nanocages or nanoshells can be used as contrast agents in optical imaging techniques such as optical coherent tomography, two-photon luminescence (TPL) microscopy, and photoacoustic imaging. Their large absorption cross-sections can also effectively convert photon energy to heat during photothermal therapy. Nanostars, which absorb in the NIR, have been hypothesized to behave similarly. Nanostar-related bioapplications remain scarce in spite of their potential, mostly due to the difficulty of surface functionalization. For example, further use of nanostars has been limited by (1) the potential toxicity of CTAB, (2) the difficulty of replacing PVP or CTAB during biofunctionalization, and (3) induction of aggregation following multiple washes. A polymer-free synthesis is provided herein to circumvent these issues.

In one embodiment of the present disclosure, a seed-mediated polymer-free synthesis method is provided for preparation of plasmonics-active gold nanostars. In one embodiment, a high-yield of monodisperse gold nanostars can be prepared having a mean tip-to-tip diameter from about 30 to about 80 nm or about 50 to about 70 nm. The nanostars of the present disclosure have plasmon bands tunable in the NIR, and the preparation method simplifies surface modification for further applications. The optical properties and plasmonic tunability of the nanostars provided herein have been experimentally examined and the results are described herein in the Examples below. The use of the nanostars as a multiphoton contrast agent during in vitro cellular imaging was also investigated and described herein in the Examples below.

In one embodiment of the present disclosure, a method is provided for preparing plasmonics-active gold nanostars (see FIG. 1 and the Examples below). The synthesis can be rapid and reproducible and may not require a polymer as surfactant.

In one embodiment of the methods provided herein, and unlike previous methods which can take longer than hours of synthesis, the growth of the gold nanostars can be completed in less than about half a minute and the particles can be stable at 4° C. for about a week after centrifugal washing. In one embodiment, the polymer-free synthesis method provided herein can simplify surface functionalization of the nanostars. In one embodiment, the plasmon peak of the nanostars can be tuned from about 600 nm to about 1000 nm in the synthesis method. Thus, in the methods according to the present disclosure, gold nanostars can be synthesized in a controlled fashion for various uses such as for example NIR applications.

One embodiment of the present disclosure comprises, consists of, or consists essentially of a plasmonics-active gold nanostar resulting from a method including: adding citrate stabilized gold seeds to a solution of tetrachloroauric acid $HAuCl_4$ under acidic conditions; and mixing a silver salt compound and a weak reducing agent simultaneously into the solution of $HAuCl_4$ under conditions such that the plasmonics-active gold nanostars are produced.

The size of the gold nano stars and the plasmon peak of the gold nanostars can be tuned. A plasmon peak of the gold nanostar can range from about 600 nm to about 1000 nm. A size of the gold nanostar can range from about 30 nm to about 80 nm.

A size of the citrate stabilized gold seeds can range from about 4 nm to about 13 nm. A concentration of the citrate stabilized gold seeds can range from about 20 μg/L to about 60 μg/L.

A concentration of the $HAuCl_4$ can range from about 0.2 to about 0.3 millimolar.

The acidic conditions can consist of a pH of less than about 5. The acidic conditions can range from a pH of about 1.5 to about pH 4. The acidic conditions can range from a pH of about 2 to about pH 3.

The weak reducing agent can consist essentially of ascorbic acid. In the method, the ratio of ascorbic acid to $HAuCl_4$, can range from about 1.5 to about 2.

The silver salt compound can consist essentially of silver nitrate ($AgNO_3$). A concentration of a silver cation of the silver compound can range from about 5 μM to about 30 μM. Increasing concentrations of the silver cation can allow for red-shifting of the plasmon peak of the gold nanostars.

In one embodiment of the present disclosure, plasmonics-active gold nanostars are provided resulting from the method wherein gold bromide ($AuBr_3$) can be substituted for the $HAuCl_4$.

In one embodiment of the present disclosure, a method is provided for preparing plasmonics-active gold nanostars, the method comprises, consists of, or consists essentially of: adding citrate stabilized gold seeds to a solution of $HAuCl_4$ under acidic conditions; and mixing a silver salt compound and a weak reducing agent simultaneously into the solution of $HAuCl_4$ under conditions such that the plasmonics-active gold nanostars are produced.

According to the method for preparing plasmonics-active gold nanostars, the size of the gold nanostars and the plasmon peak of the gold nanostars can be tuned. In the method, a plasmon peak of the gold nanostar can range from about 600 nm to about 1000 nm. In the method, a size of the gold nanostar can range from about 30 nm to about 80 nm.

In the method, the size of the citrate stabilized gold seeds can range from about 4 nm to about 13 nm. In the method, a concentration of the citrate stabilized gold seeds can range from about 20 μg/L to about 60 μg/L.

In the method, a concentration of the $HAuCl_4$ can range from about 0.2 to about 0.3 millimolar.

In the method, the acidic conditions can consist of a pH of less than about 5. In the method, the acidic conditions can range from a pH of about 1.5 to about pH 4. In the method, the acidic conditions can range from a pH of about 2 to about pH 3.

In the method, the weak reducing agent can consist essentially of ascorbic acid. In the method, the ratio of ascorbic acid to $HAuCl_4$, can range from about 1.5 to about 2.

In the method, the silver salt compound can consist essentially of silver nitrate ($AgNO_3$). In the method, a concentration of a silver cation of the silver compound can range from about 5 μM to about 30 μM. Increasing concentrations of the silver cation can allow for red-shifting of the plasmon peak.

In one embodiment of the method, gold bromide ($AuBr_3$) also can be substituted for the $HAuCl_4$.

In one embodiment of the present disclosure, a plasmon peak of the gold nanostar can range from about 600 nm to about 1000 nm and the nanostar can further include one or more of an optical or a non-optical label, a photosensitizer, a photoactivator, and a bioreceptor. Each of the optical or non-optical label, the photosensitizer, and the photoactivator can absorb electromagnetic radiation emitted by the gold nanostar when the gold nanostar is excited by a single-photon or multi-photon excitation.

The optical labels useful with the nanostars of the present disclosure can be any optical label that can absorb electromagnetic radiation emitted by the nanostar. In one embodiment, the optical label can include one or more of a fluorescence label, a fluorescein, a rhodamine, a phosphorescence label, a Raman label, a 3,3'-Diethylthiadicarbocyanine iodide (DTDC) label, a photoacoustic label, an optical coherence tomography (OCT) label, and an absorbance label.

The non-optical labels useful with the nanostars of the present disclosure can be any non-optical label that can absorb electromagnetic radiation emitted by the nanostar. The non-optical label can include one or more of a magnetic resonance imaging (MRI) label, a 1,4,7,10-Tetraazacyclododecane-1,4,7,10-tetraacetic acid (DOTA) conjugated to a contrast agent label, a positron emission tomography (PET) label, a DOTA conjugated to a PET contrast agent label, and an ultrasound label.

The photosensitizers useful with the nanostars of the present disclosure can be any photosensitizer that can absorb electromagnetic radiation emitted by the nanostar. In one embodiment, the photosensitizer can include a porphyrin, a protoporphyrin IX, or a methylene blue.

The photoactivators useful with the nanostars of the present disclosure can be any photoactivator that can absorb electromagnetic radiation emitted by the nanostar. In one embodiment, the photoactivator can include a psoralen or a psoralen variant.

The nanostars of the present disclosure can include a passivating coating to increase circulation half-life. The one or more of the optical or non-optical label, the photosensitizer, the photoactivator, and the bioreceptor can be adsorbed or covalently attached to the gold nanostar or can be embedded in a layer surrounding the gold nanostar. The layer surrounding the nanostars can consists essentially of silica, poly(N-isopropylacrylamide (pNIPAM), or polyethylene glycol (PEG). The nanostars can include a protective coating on top of the layer surrounding the nanostars.

In one embodiment, the nanostars of the present disclosure can include a drug embedded in the layer surrounding the gold nanostar such that the drug can be released or activated via one or more of passive diffusion release, photochemically triggered release, thermal triggered release, pH triggered release, photochemical activation, and thermal activation. The drug can include one or more of a drug that can be beneficial to a cell, a drug that can be detrimental to a cell, and a small interference RNA (siRNA) designed to bind to mRNA in order to trigger or prevent gene expression. The nanostars can include a spherical paramagnetic nucleus, an elongated paramagnetic nucleus, a void space nucleus, or a dielectric core.

Figure 2A:
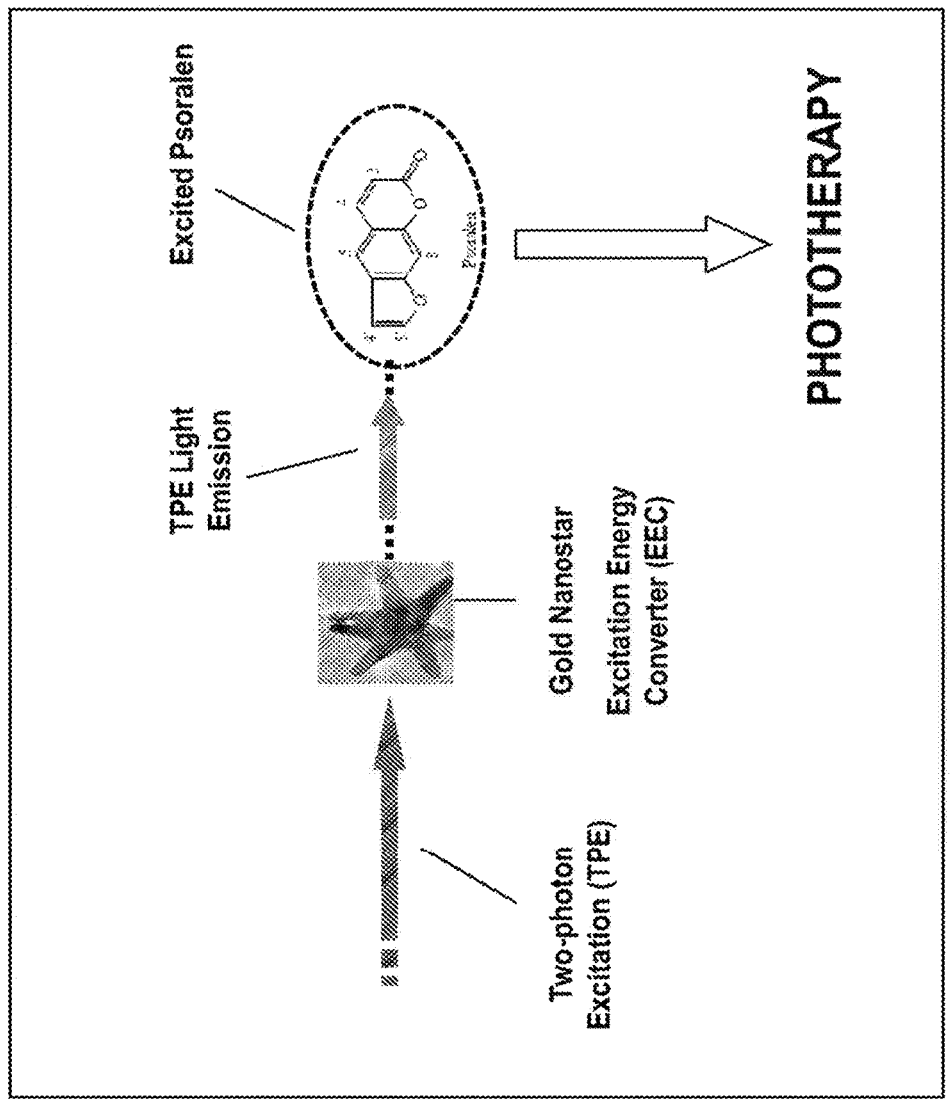
FIGS. 2A & 2B are schematic diagrams of model embodiments of a gold nanostar as the Excitation Energy Converter (EEC) according to one or more embodiments of the present disclosure. 2A) Use of a gold nanostar as the Excitation Energy Converter (EEC) using two photon excitation (TPE) to excite psoralen for phototherapy. 2B) Use of a gold nanostar (represented as a circle) as the Excitation Energy Converter (EEC) using multi-photon excitation to excite a Photo Activator (PA) for phototherapy.
Figure 2B:
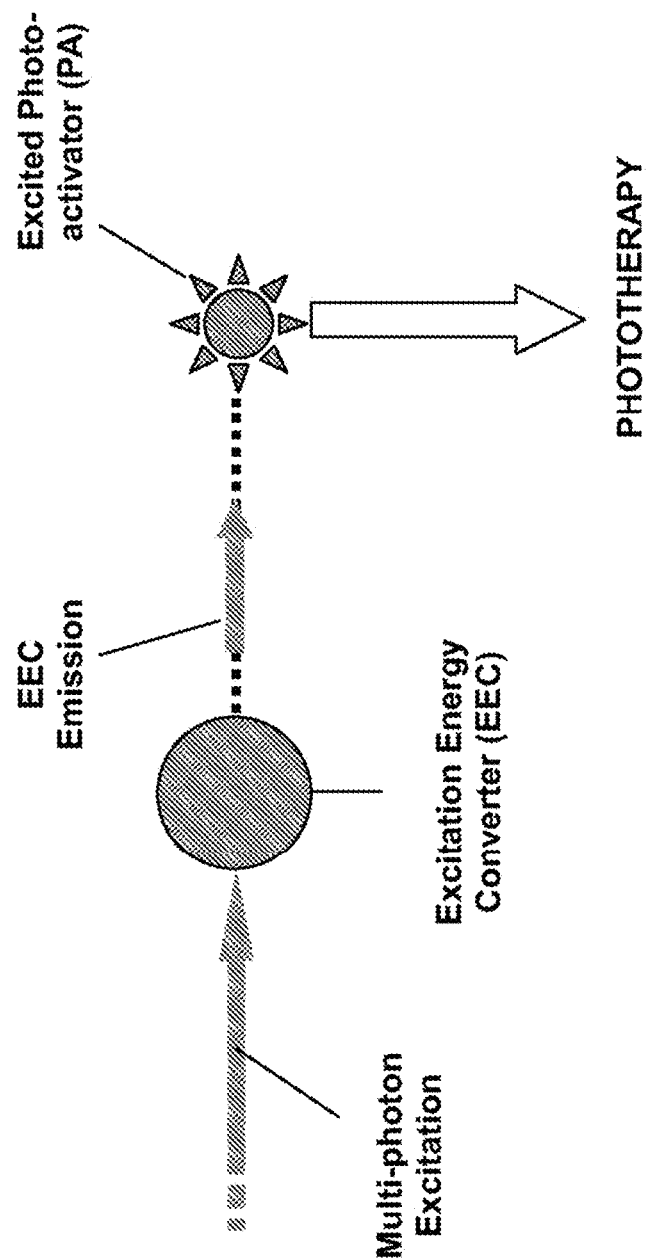

In another aspect, the present disclosure provides nanostar systems for treating cells or killing or damaging undesirable cells in vivo and ex vivo as well as detecting the cells. For example, FIGS. 2A and 2B are schematic diagrams of model embodiments of a nanostar as an Excitation Energy Converter (EEC) according to one or more embodiments of the present disclosure. FIG. 2A shows use of a gold nanostar as the EEC using two photon excitation (TPE) to excite psoralen which is a photoactivator for phototherapy. FIG. 2B shows use of a nanostar (represented as a circle) as the EEC using multi-photon excitation to excite a photo activator (PA) for phototherapy. Thus, the EEC is a nanostar of the present disclosure. In one embodiment, the nanostar is a gold nanostar. In one embodiment, the nanostar is a silver nanostar. In one embodiment, single photon excitation can be used to excite the nanostar. In one embodiment, two-photon or multi-photon excitation can be used to excite the nanostar. The terms two-photon and multi-photon excitation are herein used interchangeably. In FIGS. 2A and 2B the light emitted by the nanostar (EEC) under multi-photon excitation is used to excite the photoactivator in order to produce the therapeutic effect of the photoactivator on the cell.

Advantages of the nanostars and the methods of the present disclosure include that the nanostar does not require a down convertor or upconverter. The gold nanostars serve both as the plasmonic enhancer and the EEC emitter. The gold nanostars can be non-toxic and biocompatible materials. The nanostar compositions and methods of the present disclosure can produce both therapy and diagnostics (theranostics). The photonics treatment modalities of the present disclosure can include both optical and non-optical technologies that involve electromagnetic radiation ranging from gamma rays and X rays throughout ultraviolet, visible, infrared, microwave and radio frequency energy.

Figure 3:
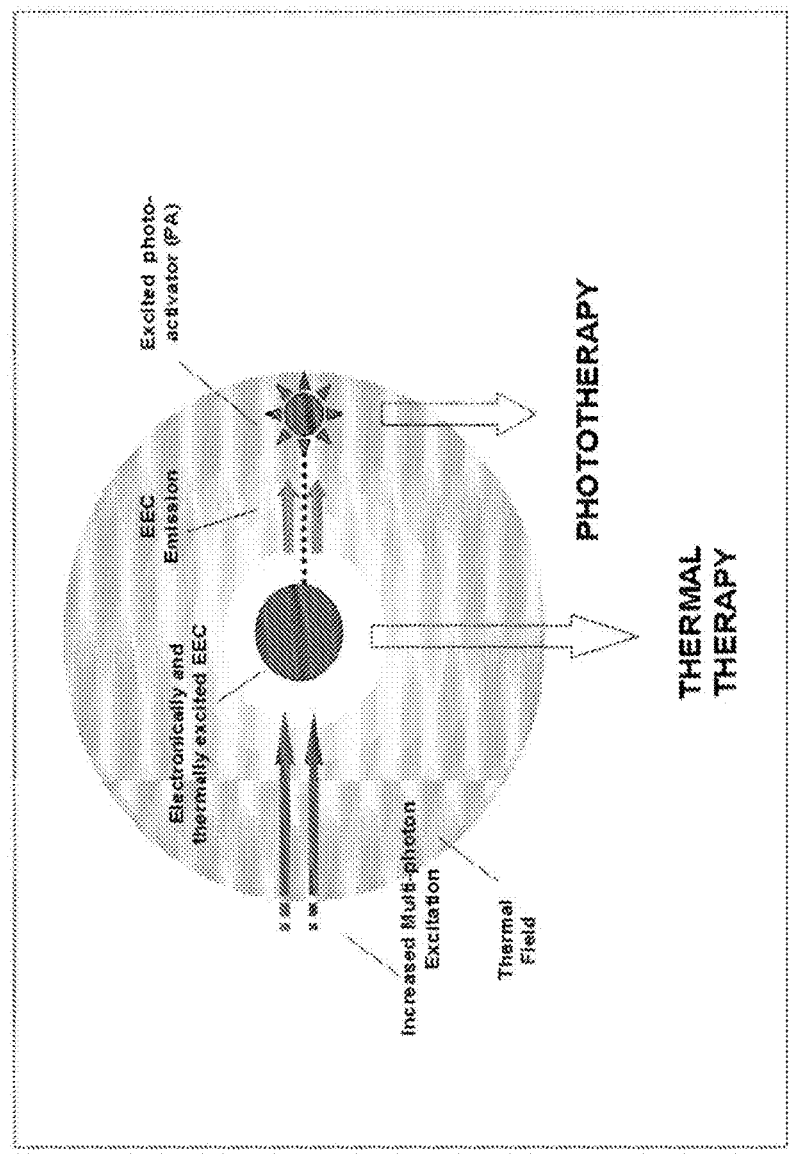
FIG. 3 is a schematic diagram of a multi-photon multi-modality therapy that is a combination of phototherapy and thermal therapy according to one or more embodiments of the present disclosure.

FIG. 3 is shows a schematic diagram of a multi-photon multimodality therapy that is a combination of phototherapy and thermal therapy according to one or more embodiments of the present disclosure. Advantages of the nanostar nanoplatforms of the present disclosure include: 1) multi-photon excitation allows for deep tissue excitation which can be referred to as the "therapeutic window"; 2) increased absorption of the excitation light by the plasmonic metal nanostar nanoplatforms can result in enhanced function for therapy and detection; 3) increased absorption of the excitation light by the plasmonic metal nanostar nanoplatforms yield more light for excitation of optical and non-optical labels such as, for example, Raman and fluorescence labels; 4) increased absorption of the excitation light by the plasmonic metal nanostars results in increased heating of the nanostars such as, for example, for improved thermolysis; 5) increased absorption of the excitation light by optical dye labels, such as, for example, Raman, fluorescent, and phosphorescent labels, adsorbed or covalently attached on or near the plasmonic metal nanostar; 6) increased light absorption of a dye label adsorbed on or near the metal nanostars; 7) amplified emission from a dye label and/or a phototherapeutic molecule such as, for example, psoralen adsorbed on or near the metal nanostars, leading to enhanced phototherapy; 8) a photothermal effect produced by the nanostars under multi-photon excitation; and 9) a combination of enhanced detection and enhanced therapy via the above nanostar processes.

Figure 4:
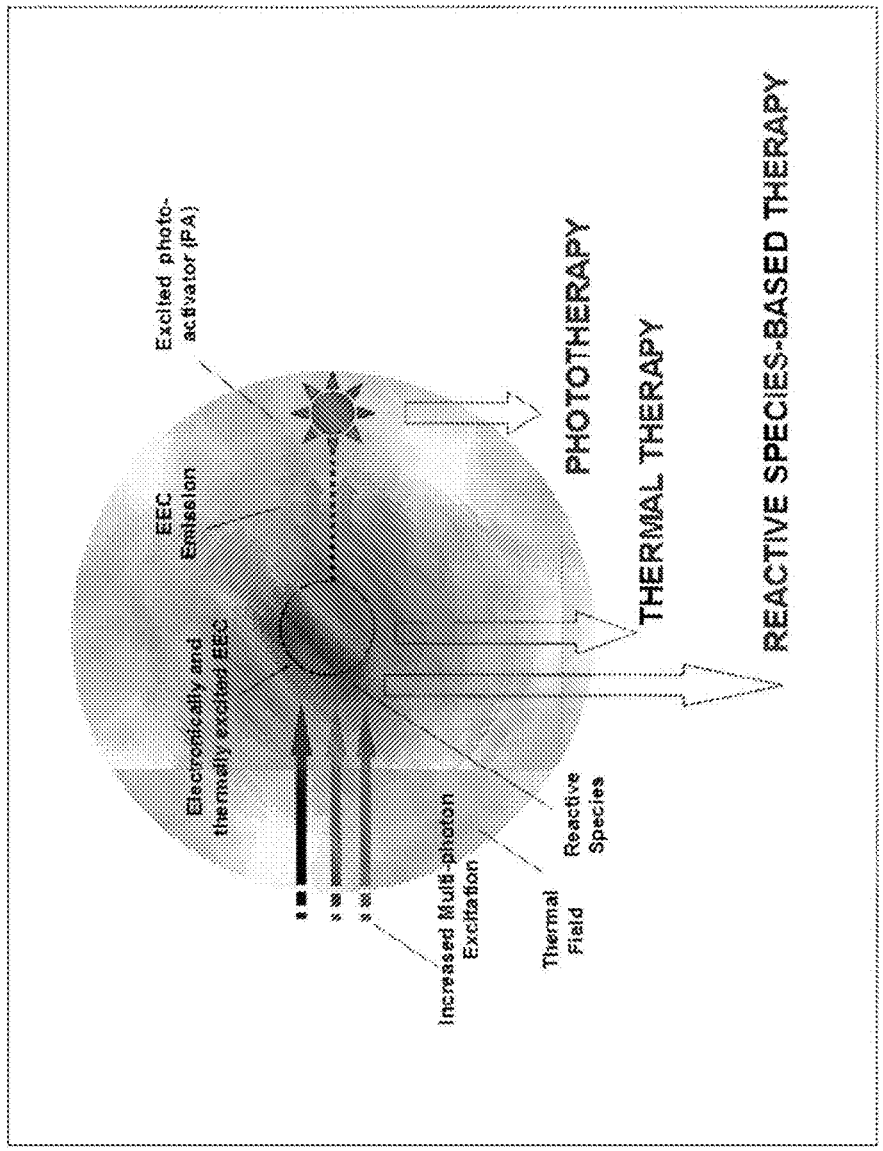
FIG. 4 is a schematic diagram of a multi-photon multi-modality therapy that is a combination of phototherapy and thermal therapy and reactive species according to one or more embodiments of the present disclosure.

In another embodiment, multi-photon excitation of the metal nanostars can also produce reactive species, which can kill nearby cells, thus providing an additive therapeutic modality (see FIG. 4). FIG. 4 a schematic diagram of a multi-photon multimodality therapy that is a combination of phototherapy and thermal therapy and reactive species according to one or more embodiments of the present disclosure.

Figure 5:
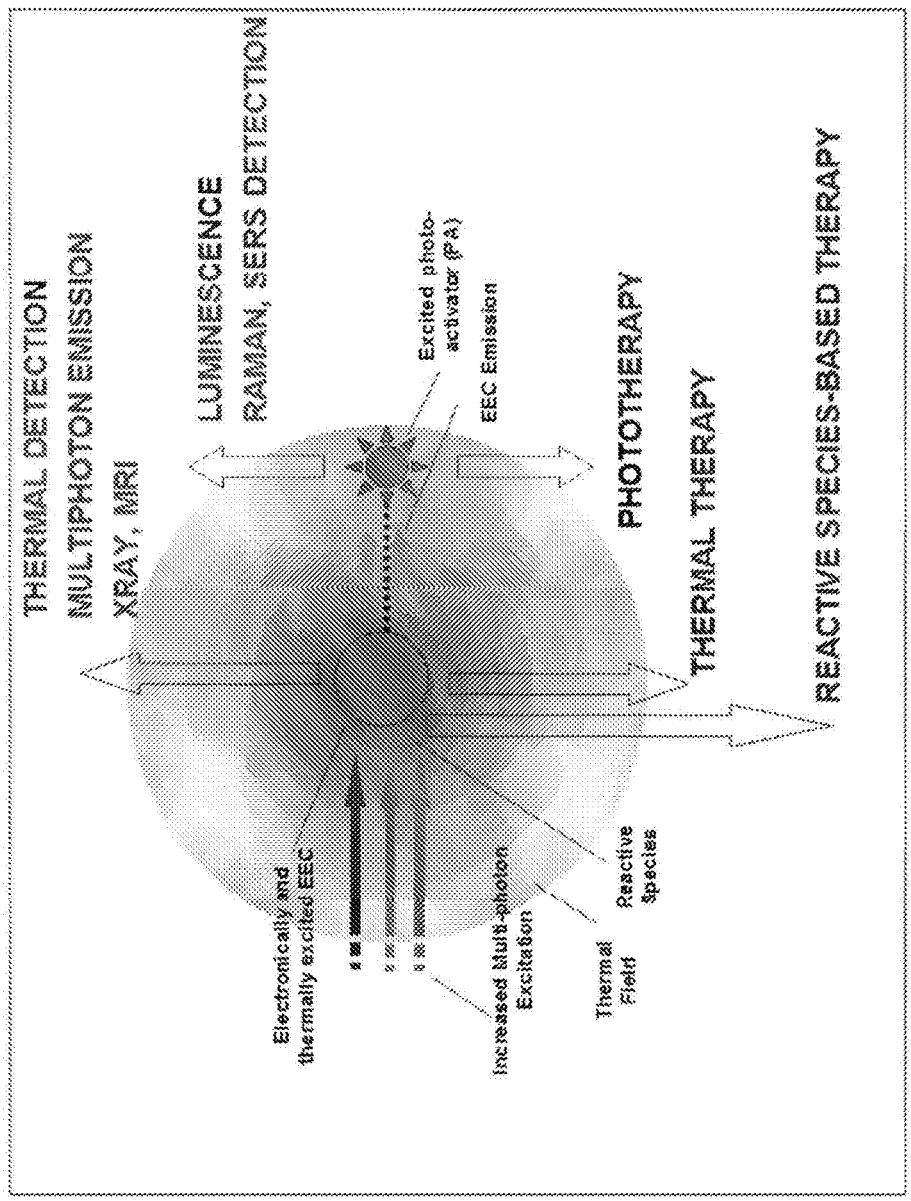
FIG. 5 is a schematic diagram of a multi-photon multi-modality therapy, detection and diagnostics according to one or more embodiments of the present disclosure.

In another embodiment depicted in FIG. 5, the multi-photon excitation of the metal nanostars of the present disclosure can be used for detection as well as for treatment as follows: 1) the nanostars can be used as contrast agents that can be detected by techniques including but not limited to thermal detection, multi-photon excited emission, X-ray, MRI, photoacoustic, and optical coherence tomography; 2) the photoactivator included with the nanostar, such as psoralen, can be detected by techniques including but not limited to Raman, SERS, and fluorescence.

Figure 6A:
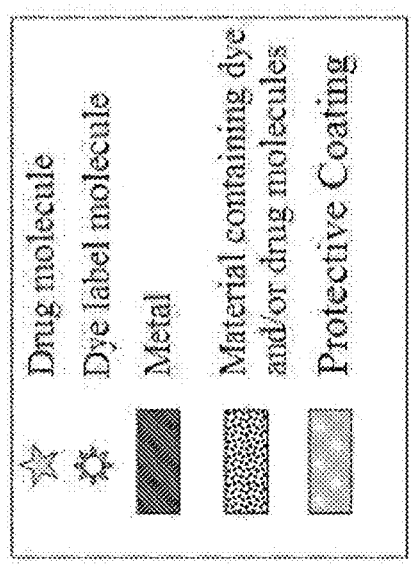
FIGS. 6A-6I are schematic diagrams showing a series of plasmonics-active nanostars according to one or more embodiments of the present disclosure. 6A-6H show the plasmonics-active nanostars and 6I shows the legend.
Figure 6B:
Figure 6C:
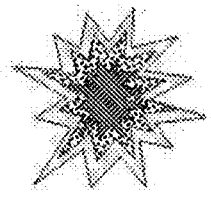
Figure 6D:
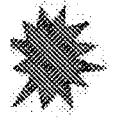
Figure 6E:
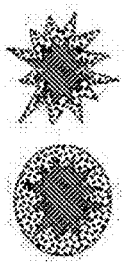
Figure 6F:
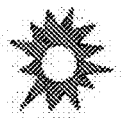
Figure 6G:
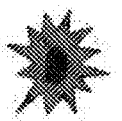
Figure 6H:
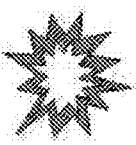
Figure 6I:
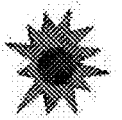

FIGS. 6A-6H are schematic diagrams showing various plasmonics-active nanostars according to one or more embodiments of the present disclosure. FIG. 6I shows the legend for FIGS. 6A-6H. FIG. 6A shows a plasmonics-active nanostar. FIG. 6B shows the nanostar labeled with optical dye and/or a drug molecule. FIG. 6C shows the nanostar having a layer embedded with a label and/or a drug (e.g., psoralen). FIG. 6D shows the nanostar with a layer embedded with a label and/or drug (e.g., psoralen) and a protective overlayer. FIG. 6E shows the nanostar with a paramagnetic spherical nucleus. FIG. 6F shows the nanostar with an elongated paramagnetic nucleus. FIG. 6G shows the nanostar having a void-space. FIG. 6H shows the nanostar having an empty or dielectric core.

In another aspect of the present disclosure, the nanostars can include bioreceptors that can be used for specificity for targeting disease cells. The bioreceptors can be responsible for binding the nanostar to the biotarget of interest for therapy. These bioreceptors can take many forms and the different bioreceptors that can be used are as numerous as the different analytes that have been monitored using biosensors. Bioreceptors can generally be classified into five different major categories. These categories include: 1) antibody/antigen, 2) enzymes, 3) nucleic acids/DNA, 4) cellular structures/cells and 5) biomimetic (aptamers, peptides, etc).

FIGS. 7A-7H are schematic diagrams showing various plasmonics-active nanostars with bioreceptor according to one or more embodiments of the present disclosure. FIG. 7I shows the legend for FIGS. 7A-6H. The nanostars shown in FIGS. 7A-7H are similar to those shown in FIGS. 6A-H but also have a bioreceptor for targeting to a specific cell or a tumor. FIG. 7A shows a plasmonics-active nanostar with bioreceptor. FIG. 7B shows the nanostar labeled with optical dye and/or a drug molecule with bioreceptor. FIG. 7C shows the nanostar having a layer embedded with a label and/or a drug (e.g., psoralen) with bioreceptor. FIG. 7D shows the nanostar with a layer embedded with a label and/or drug (e.g., psoralen) and a protective overlayer with bioreceptor. FIG. 7E shows the nanostar with a paramagnetic spherical nucleus with bioreceptor. FIG. 7F shows the nanostar with an elongated paramagnetic nucleus with bioreceptor. FIG. 7G shows the nanostar having a void-space with bioreceptor. FIG. 7H shows the nanostar having an empty or dielectric core with bioreceptor.

To specifically target diseases cells, specific genes or protein markers, the nanostars of the present disclosure can be bound to a bioreceptor (e.g., antibody, DNA, proteins, cell-surface receptors, aptamers, etc.) as described above. A general description of certain of the bioreceptors is provided below.

DNA Probes. The operation of gene probes is based on the hybridization process. Hybridization involves the joining of a single strand of nucleic acid with a complementary probe sequence. Hybridization of a nucleic acid probe to DNA biotargets (e.g., gene sequences of a mutation, etc) offers a very high degree of accuracy for identifying DNA sequences complementary to that of the probe. Biologically active DNA probes can be directly or indirectly immobilized onto a drug system, such as the EEC system (e.g., gold nanoparticle, a semiconductor, quantum dot, a glass/quartz nanoparticles, etc.) surface to ensure optimal contact and maximum binding. When immobilized onto nanoparticles including nanostars, the gene probes are stabilized and, therefore, can be reused repetitively. Several methods can be used to bind DNA to different supports. The method commonly used for binding DNA to glass involves silanization of the glass surface followed by activation with carbodiimide or glutaraldehyde. The silanization method can be used for binding to glass surfaces using 3-glycidoxypropyltrimethoxysilane (GOP) or aminopropyltrimethoxysilane (APTS) to covalently link DNA via amino linkers incorporated either at the 3' or 5' end of the molecule during DNA synthesis.

Antibody Probes. Antibodies are biological molecules that exhibit very specific binding capabilities for specific structures and that can be used as bioreceptors. This unique property of antibodies is the key to their usefulness in immunosensors where only the specific analyte of interest, the antigen, fits into the antibody binding site.

Enzyme Probes. Enzymes are often chosen as bioreceptors based on their specific binding capabilities as well as their catalytic activity. In biocatalytic recognition mechanisms, the detection is amplified by a reaction catalyzed by macromolecules called biocatalysts. The catalytic activity provided by enzymes allows for much lower limits of detection than would be obtained with common binding techniques. Enzyme-coupled receptors can also be used to modify recognition mechanisms.

Other approaches. Methods for conjugation of nanostars with receptor-binding molecules can be used that can selectively increase the adherence or uptake of nanostars for targeting cells. In addition to bioreceptor molecules such as antibodies, antibody fragments, and DNA/RNA aptamers, peptides can also be used since they offer several advantages as bioreceptors for nanostars (low cost, high activity per unit, excellent stability, long-term storage and easy handling). An enzyme-mediated process can also be used for targeting. Overexpression of certain enzymes at the site of disease can be used for the development of enzyme-responsive nanoplatforms diagnosis. For in vivo models, it is also important keep the nanoparticles out of the blood circulation to prevent clearance. The concept of using iron oxide-gold core-shell particles, can provide a unique solution. The gold shell will allow for the same functionalization methods to be used from the ex vivo work, while the iron oxide core will be superparamagnetic. A magnet can be used to collect and keep the particles at one location in the body, at which the analysis can be performed. The iron oxide core can provide for multimodality diagnostics (SERS, luminescence, MRI) and co-registration.

Bioreceptors (and other biomolecules) as well as drug molecules can be immobilized to a solid support such as a metal nanostar using a wide variety of methods published in the literature. Binding can be performed through covalent bonds by taking advantage of reactive groups such as amine ($-NH_2$) or sulfide ($-SH$) that are naturally present or can be incorporated into the bioreceptor/biomolecule structure. For example, amines can react with carboxylic acid or ester moieties in high yield to form stable amide bonds. Thiols can participate in maleimide coupling, yielding stable dialkylsulfides.

A solid support of interest is gold (or silver) nanostars according to the present disclosure. The majority of immobilization schemes involving Au(Ag) surfaces utilize a prior derivatization of the surface with alkylthiols, forming stable linkages. Alkylthiols readily form self-assembled monolayers (SAM) onto silver surfaces in micromolar concentrations. The terminus of the alkylthiol chain can be used to bind biomolecules, or can be easily modified to do so. The length of the alkylthiol chain has been found to be an important parameter, keeping the biomolecules away from the surface. Furthermore, to avoid direct, non-specific DNA adsorption onto the surface, alkylthiols have been used to block further access to the surface, allowing only covalent immobilization through the linker.[56, 57]

Silver surfaces have been found to exhibit controlled self-assembly kinetics when exposed to dilute ethanolic solutions of alkylthiols. The tilt angle formed between the surface and the hydrocarbon tail ranges from 0 to 15°. There is also a larger thiol packing density on silver, when compared to gold.[58] After SAM formation on gold/silver nanoparticles, alkylthiols can be covalently coupled to biomolecules. The majority of synthetic techniques for the covalent immobilization of biomolecules utilize free amine groups of a polypeptide (enzymes, antibodies, antigens, etc) or of amino-labeled DNA strands, to react with a carboxylic acid moiety forming amide bonds. As a general rule, a more active intermediate (labile ester) is first formed with the carboxylic acid moiety and in a later stage reacted with the free amine, increasing the coupling yield. Coupling procedures that may be used are described below.

Binding Procedure Using N-hydroxysuccinimide (NHS) and its derivatives. The coupling approach involves the esterification under mild conditions of a carboxylic acid with a labile group, an N-hydroxysuccinimide (NHS) derivative, and further reaction with free amine groups in a polypeptide (enzymes, antibodies, antigens, etc) or amine-labeled DNA, producing a stable amide.[59] NHS reacts almost exclusively with primary amine groups. Covalent immobilization can be achieved in as little as 30 minutes. Since $H_2O$ competes with —NH$_2$ in reactions involving these very labile esters, it is important to consider the hydrolysis kinetics of the available esters used in this type of coupling. Use of the derivative of NHS O—(N-succinimidyl)-N,N,N',N'-tetramethyluronium tetrafluoroborate, increases the coupling yield by utilizing a leaving group that is converted to urea during the carboxylic acid activation, hence favorably increasing the negative enthalpy of the reaction.

Binding Procedure Using Maleimide. Maleimide can be used to immobilize biomolecules through available —SH moieties. Coupling schemes with maleimide have been proven useful for the site-specific immobilization of antibodies, Fab fragments, peptides, and SH-modified DNA strands. Sample preparation for the maleimide coupling of a protein involves the simple reduction of disulfide bonds between two cysteine residues with a mild reducing agent, such as dithiothreitol, 2-mercaptoethanol or tris(2-carboxyethyl)phosphine hydrochloride. However, disulfide reduction will usually lead to the protein losing its natural conformation, and might impair enzymatic activity or antibody recognition. The modification of primary amine groups with 2-iminothiolane hydrochloride (Traut's reagent) to introduce sulfydryl groups is an alternative for biomolecules lacking them. Free sulfhydryls are immobilized to the maleimide surface by an addition reaction to unsaturated carbon-carbon bonds.[60]

Binding Procedure Using Carbodiimide. Surfaces modified with mercaptoalkyldiols can be activated with 1,1'-carbonyldiimidazole (CDI) to form a carbonylimidazole intermediate. A biomolecule with an available amine group displaces the imidazole to form a carbamate linkage to the alkylthiol tethered to the surface.[61]

The nanostars can be used for therapy as well as for diagnostics since gold nanoparticles have been shown to be a candidate for contrast agents for X-ray.[62] The concept of using high-Z materials for dose enhancement in cancer radiotherapy was advanced over 20 years ago. The use of gold nanoparticles as dose enhancer is advantages over prior art methods for two primary reasons. First, gold has a higher Z number than iodine (I, Z=53) or gadolinium (Gd, Z=64), while showing little toxicity, up to at least 3% by weight, on either rodent or human tumour cells. Gold nanoparticles have been shown to be non-toxic to mice and largely cleared from the body through the kidneys. This use of small gold nanoparticles permitted achievement of the high metal content in tumours necessary for significant high-Z radioenhancement.[63]

Delivering a lethal dose of radiation to a tumour while minimizing radiation exposure of nearby normal tissues remains the greatest challenge in radiation therapy. The dose delivered to a tumour during photon-based radiation therapy can be enhanced by loading high atomic number (Z) materials such as gold (Au, Z=79) into the tumor, resulting in greater photoelectric absorption within the tumor than in surrounding tissues. Thus, gold clearly leads to a higher tumor dose than either iodine or gadolinium. Second, nanoparticles provide a better mechanism than microspheres, in terms of delivering high-Z materials to the tumor, overcoming some of the difficulties found during an earlier attempt using gold microspheres.[64]

In one embodiment, the nanostars of the present disclosure can include a bioreceptor. The bioreceptor can be one or more of a peptide, a cell penetrating peptide (CPP), a Human immunodeficiency virus type 1 (HIV-1) Trans-Activator of Transcription (TAT) peptide, a MAP peptide, angiopep2 peptide, a cRGD peptide, transferrin, an antibody, a HER2 antibody, a HERCEPTIN® antibody (Trastuzumab antibody), anti-EGRF antibody, a nucleic acid, a DNA, a cell surface receptor, and an aptamer. In one embodiment, the bioreceptor is a TAT peptide.

Figure 8B:
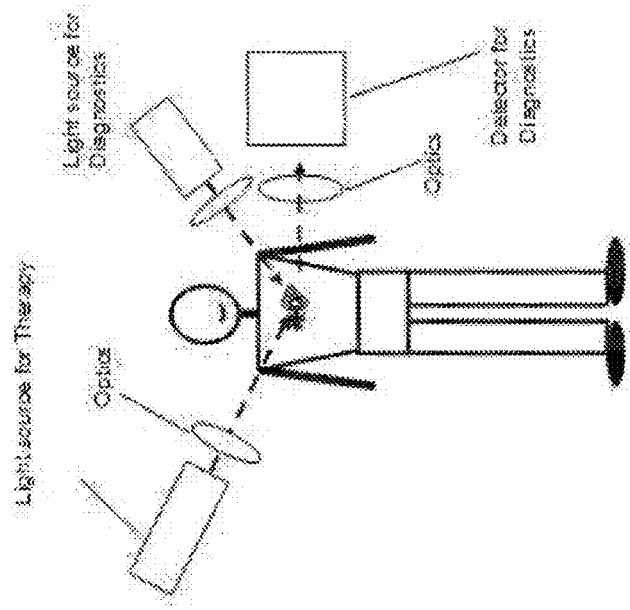
FIGS. 8A-8B are schematic diagrams showing a non-invasive use of a psoralen-functionalized nanostar (MMTD drug) for therapy and diagnostics according to one or more embodiments of the present disclosure.
Figure 8A:
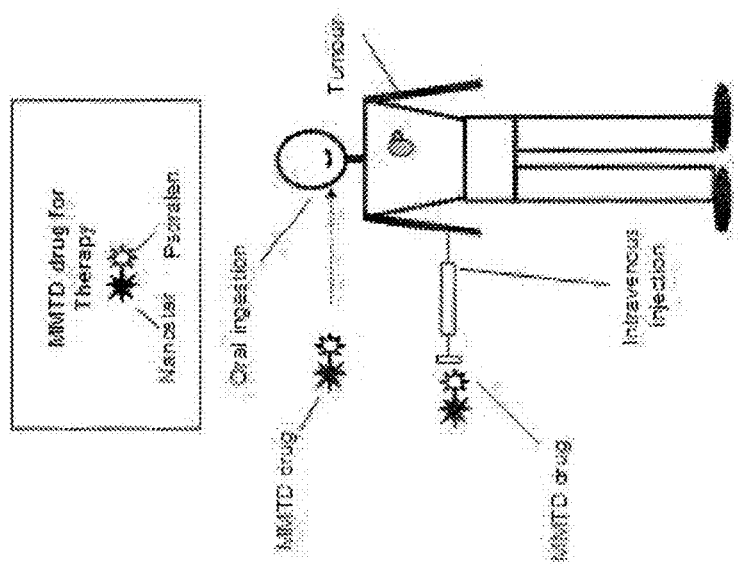

FIGS. 8A-8B are schematic diagrams showing the non-invasive use of a psoralen-functionalized nanostar for therapy and diagnostics according to one or more embodiments of the present disclosure. In this embodiment, gold nanostars functionalized with the photoactivator psoralen (represented as MMTD drug in FIGS. 8A and 8B) can be administered to a patient by oral ingestion or by intravenous injection. The figures depict the MMTD drug traveling through the blood stream inside the body towards the targeted tumor (either via passive or active targeting strategies). If the disease is systematic in nature a photon radiation at a suitable wavelength such as, for example, radio frequency (RF), microwave (MW), infra red (IR), NIR, VIS, UV, and X ray can be used to irradiate the skin of the patient, the light being selected to penetrate deep inside the patient's tissue (e.g., NIR). For solid tumors, the radiation light source can be directed at the tumor. Subsequently, a treatment procedure can be initiated using delivery of energy into the tumor site. One or several light sources may be used as described in the previous sections. One example of therapy consists of sending NIR radiation using an NIR laser through focusing optics. The heat can be used to kill diseased cells or tissues. Alternatively, the heat can be used to release psoralen (or another drug of choice).

Table 1 shows some examples of the plasmonics-active nanostar methods of the present disclosure that combine diagnostics and therapy (Theranostics) using optical and non-optical techniques.

TABLE 1

Examples of Theranostics Methods

| Detection Methods | Treatment Methods | | |
| --- | --- | --- | --- |
| | Phototherapy (e.g., Psoralen) | Photothermal therapy | Other optical treatments (e.g., ROS) |
| Fluorescence (1-p, 2-p, multi-p) | x | x | x |
| Phosphorescence | x | x | x |
| Raman | x | x | x |
| Diffuse Scattering | x | x | x |
| Absorption | x | x | x |
| Optical Coherence Methods | x | x | x |
| Photoacoustics | x | x | x |
| X-ray | x | x | x |
| MRI | x | x | x |
| PET | x | x | x |

Focused beam or other radiation including but not limited to such as, for example, X ray, MW, and RF can also be used and will depend upon the treatment methods used. For X-ray excitation, the core of the nanostars can consist of materials that exhibit X-ray excited luminescence (XEOL). There is a wide variety of materials that exhibit XEOL including but not limited to such as, for example, organic, inorganic solids, crystals, lanthanides, polymers.

In one embodiment, a method is provided for treating undesirable cells in a subject. The method includes administering to a subject a plasmonics-active gold or silver nanostar having a bioreceptor, such that the bioreceptor can target the nanostar to an undesirable cell. In addition to the bioreceptor, the nanostar also has one or both of a photosensitizer and a photoactivator. The photosensitizer and a photoactivator each can absorb electromagnetic radiation emitted by the gold nanostar when the nanostar is excited by a single-photon or multi-photon excitation. The methods also includes applying the single photon or multi-photon excitation to the subject such that the nanostar is excited and emits electromagnetic radiation that is absorbed by the photosensitizer and the photoactivator. In this manner, the undesirable cell can be damaged or killed by one or a combination of thermal energy emitted by the nanostar, reactive oxygen species (ROS) generated by the photosensiter, and one or a combination of activation and release of the photoactivator.

In one embodiment, an ex vivo method of treating undesirable cells is provided including: contacting ex vivo a group of cells comprising an undesirable cell with a plasmonics-active gold or silver nanostar having: a bioreceptor, wherein the bioreceptor targets the nanostar to the undesirable cell; and one or more of a photosensitizer and a photoactivator, wherein the photosensitizer and the photoactivator absorb electromagnetic radiation emitted by the nanostar when the nanostar is excited by a single photon or multi-photon excitation; and applying the single-photon or multi-photon excitation to the group of cells such that the nanostar is excited and emits electromagnetic radiation that is absorbed by the photosensitizer and the photoactivator such that the undesirable cell is damaged by one or a combination of thermal energy emitted by the nanostar, reactive oxygen species (ROS) generated by the photosensiter, and one or a combination of activation and release of the photoactivator.

The photosensitizers useful with the methods for treating cells can be any suitable photosensitizer that can absorb electromagnetic radiation emitted by the nanostar. In one embodiment, the photosensitizer can include a porphyrin, a protoporphyrin IX, or a methylene blue.

The photoactivators useful with the methods for treating cells can be any suitable photoactivator that can absorb electromagnetic radiation emitted by the nanostar. In one embodiment, the photoactivator can include a psoralen or a psoralen variant.

In one embodiment of the methods for treating cells, the nanostars can include a drug embedded in the layer surrounding the gold nanostar such that the drug can be released or activated via one or more of passive diffusion release, photochemically triggered release, thermal triggered release, pH triggered release, photochemical activation, and thermal activation. In one embodiment of the methods for treating cells, all or a portion of the cells are desirable rather than undesirable and the drug can include one or more of a drug that can be beneficial to the cells, a drug that can be detrimental to the cells, and a small interference RNA (siRNA) designed to bind to mRNA in order to trigger or prevent gene expression in the cells. In one embodiment of the methods for treating cells, the nanostars can include a spherical paramagnetic nucleus, an elongated paramagnetic nucleus, a void space nucleus, or a dielectric core. In one embodiment, the paramagnetic nucleus or the dielectric core can be used to target the drug to the cells. In one embodiment, the drug molecule can be placed within the void space to deliver the drug to the cells.

In one embodiment of the methods for treating cells, the method further includes detecting the electromagnetic radiation emitted by the nanostar by one or more of X-ray, MRI, thermal detection, multi-photon emission, PET, photoacoustics, optical coherence tomography (OCT), absorption, and diffuse scattering.

In one embodiment of the methods for treating cells, the plasmonics-active nanostar further comprises an optical or a non-optical label that absorbs electromagnetic radiation emitted by the nanostar when the nanostar is excited by the single photon or multi-photon excitation such that the optical or non-optical label emits detectable electromagnetic radiation.

The optical labels useful with the methods for treating cells can be any optical label that can absorb electromagnetic radiation emitted by the nanostar. In one embodiment, the optical label can include one or more of a fluorescence label, a fluorescein, a rhodamine, a phosphorescence label, a Raman label, a 3,3'-Diethylthiadicarbocyanine iodide (DTDC) label, a photoacoustic label, an optical coherence tomography (OCT) label, and an absorbance label.

The non-optical labels useful with the methods for treating cells can be any non-optical label that can absorb electromagnetic radiation emitted by the nanostar. The non-optical label can include one or more of a magnetic resonance imaging (MRI) label, a 1,4,7,10-Tetraazacy-clododecane-1,4,7,10-tetraacetic acid (DOTA) conjugated to a contrast agent label, a positron emission tomography (PET) label, a DOTA conjugated to a PET contrast agent label, and an ultrasound label.

In one embodiment of the methods for treating cells, the optical label can include one or more of a fluorescence label, a Fluorescein, a Rhodamine, a phosphorescence label, a Raman label, a 3,3'-Diethylthiadicarbocyanine iodide (DTDC) label, a photoacoustic label, an optical coherence tomography (OCT) label, and an absorbance label, and the method can further include: detecting the electromagnetic radiation emitted by the optical label by one or more of fluorescence detection, phosphorescence detection, surface enhanced Raman scattering (SERS) detection, and absorbance detection.

In one embodiment of the methods, the non-optical label can include one or more of a magnetic resonance imaging (MRI) label, a 1,4,7,10-Tetraazacy-clododecane-1,4,7,10-tetraacetic acid (DOTA) conjugated to a contrast agent label, a positron emission tomography (PET) label, a DOTA conjugated to a PET contrast agent label, and an ultrasound label, and the method can further include: detecting the electromagnetic radiation emitted by the non-optical label by one or more of X-ray detection, MRI detection, thermal detection, multi-photon emission detection, PET detection, photoacoustics detection, OCT detection, and diffuse scattering detection.

In any of the methods for treating cells disclosed herein, the plasmonics-active nanostar can be a gold nanostar resulting from a process including: adding citrate stabilized gold seeds to a solution of $HAuCl_4$ under acidic conditions; and mixing a silver salt compound and a weak reducing agent simultaneously into the solution of $HAuCl_4$ under conditions such that the plasmonics-active gold nanostars are produced. The size of the gold nanostars and the plasmon peak of the gold nanostars can be tuned. A plasmon peak of the gold nanostar can range from about 600 nm to about 1000 nm. A size of the gold nanostar can range from about 30 nm to about 80 nm. A size of the citrate stabilized gold seeds can range from about 4 nm to about 13 nm. A concentration of the citrate stabilized gold seeds can range from about 20 µg/L to about 60 µg/L. A concentration of the $HAuCl_4$ can range from about 0.2 to about 0.3 millimolar. The acidic conditions can consist of a pH of less than about 5. The acidic conditions can range from a pH of about 1.5 to about pH 4. The acidic conditions can range from a pH of about 2 to about pH 3. The weak reducing agent can consist essentially of ascorbic acid. In the method, the ratio of ascorbic acid to $HAuCl_4$, can range from about 1.5 to about 2. The silver salt compound can consist essentially of silver nitrate ($AgNO_3$). A concentration of a silver cation of the silver compound can range from about 5 µM to about 30 µM. Increasing concentrations of the silver cation can allow for red-shifting of the plasmon peak of the gold nanostars. In one embodiment of the present disclosure, plasmonics-active gold nanostars are provided resulting from the method wherein gold bromide ($AuBr_3$) can be substituted for the $HAuCl_4$.

In one embodiment of the methods for treating cells, the bioreceptor can be one or more of a peptide, a cell penetrating peptide (CPP), a Human immunodeficiency virus type 1 (HIV-1) Trans-Activator of Transcription (TAT) peptide, a MAP peptide, angiopep2 peptide, a cRGD peptide, transferrin, an antibody, a HER2 antibody, a HERCEPTIN® antibody (Trastuzumab antibody), anti-EGRF antibody, a nucleic acid, a DNA, a cell surface receptor, and an aptamer. In one embodiment of the methods for treating cells, the bioreceptor is a TAT peptide.

In one embodiment of the methods for treating cells, the nanostars can include a passivating coating to increase circulation half-life. The one or more of the optical or non-optical label, the photosensitizer, the photoactivator, and the bioreceptor can be adsorbed or covalently attached to the nanostar or can be embedded in a layer surrounding the nanostar. The layer surrounding the nanostars can consist essentially of silica, poly(N-isopropylacrylamide (pNIPAM), or polyethylene glycol (PEG). The nanostars can include a protective coating on top of the layer surrounding the nanostars.

In one embodiment, a method is provided for treating undesirable cells in a subject including: administering to a subject a plasmonics-active gold or silver nanostar comprising a bioreceptor, wherein the bioreceptor targets the nanostar to an undesirable cell; and applying a single-photon or multi-photon excitation to the subject such that the nanostar is excited and the undesirable cell is damaged by thermal energy emitted as a result of excitation of the nanostar.

In one embodiment, an ex vivo method is provided for treating undesirable cells including: contacting ex vivo a group of cells comprising an undesirable cell with a plasmonics-active gold or silver nanostar including a bioreceptor, wherein the bioreceptor targets the nanostar to the undesirable cell; and applying a single-photon or multi-photon excitation to the group of cells such that the nanostar is excited and the undesirable cell is damaged by thermal energy emitted as a result of excitation of the nanostar.

The methods can further include detecting the electromagnetic radiation emitted by the nanostar by one or more of X-ray, MRI, thermal detection, multi-photon emission, PET, photoacoustics, optical coherence tomography (OCT), and diffuse scattering.

In the methods, the plasmonics-active nanostar can further include an optical or a non-optical label that absorbs electromagnetic radiation emitted by the nanostar when the nanostar is excited by the single photon or multi-photon excitation such that the optical or non-optical label emits detectable electromagnetic radiation.

In the methods, the optical label can include one or more of a fluorescence label, a fluorescein, a rhodamine, a phosphorescence label, a Raman label, a 3,3'-Diethylthiadicarbocyanine iodide (DTDC) label, a photoacoustic label, an optical coherence tomography (OCT) label, and an absorbance label, and the method can further include: detecting the electromagnetic radiation emitted by the optical label by one or more of fluorescence detection, phosphorescence detection, surface enhanced raman scattering (SERS) detection, and absorbance detection.

In the methods, the non-optical label can include one or more of a magnetic resonance imaging (MRI) label, a 1,4,7,10-Tetraazacy-clododecane-1,4,7,10-tetraacetic acid (DOTA) conjugated to a contrast agent label, a positron emission tomography (PET) label, a DOTA conjugated to a PET contrast agent label, and an ultrasound label, and the method can further include: detecting the electromagnetic radiation emitted by the non-optical label by one or more of X-ray detection, MRI detection, thermal detection, multi-photon emission detection, PET detection, photoacoustics detection, OCT detection, and diffuse scattering detection.

In the methods, the single-photon or multi-photon excitation can be applied to the subject at an irradiance of about 0.2-0.4 $W/cm^2$ at about 700-900 nm.

In one embodiment, a method is provided for treating undesirable cells in a subject including: administering to a subject a plasmonics-active gold or silver nanostar comprising: one or more of a photosensitizer and a photoactivator, wherein the photosensitizer and the photoactivator absorb electromagnetic radiation emitted by the gold nanostar when the nanostar is excited by a single-photon or multi-photon excitation; and applying the single photon or multi-photon excitation to the subject such that the nanostar is excited and emits electromagnetic radiation that is absorbed by the photosensitizer and the photoactivator such that the undesirable cell is damaged by one or a combination of thermal energy emitted by the nanostar, reactive oxygen species (ROS) generated by the photosensiter, and one or a combination of activation and release of the photoactivator.

One embodiment of the present disclosure comprises, consists of, or consists essentially of a method of treating undesirable cells in a subject wherein the photo-activated drug is psoralen or a psoralen variant.

Another embodiment of the present disclosure comprises, consists of, or consists essentially of a method of treating undesirable cells in a subject wherein the photo-activated drug is attached to the nanostar particles.

Yet another embodiment of the present disclosure comprises, consists of, or consists essentially of a method of treating undesirable cells in a subject wherein the photo-activated drug is embedded within a matrix around the nanostar, wherein the matrix may comprise the drug itself.

Another object of the present disclosure comprises, consists of, or consists essentially of a method of treating undesirable cells in a subject comprising: administering to the subject nanostar particles and a thermally-activated drug; and irradiating the nanostar whereby the nanostar emits a thermal response which activates the thermally-activated drug.

One embodiment of the present disclosure comprises, consists of, or consists essentially of a method of treating undesirable cells in a subject wherein the thermally-activated drug is attached to the nanostar particles.

Yet another embodiment of the present disclosure comprises, consists of, or consists essentially of a method of treating undesirable cells in a subject wherein the thermally-activated drug is embedded within a matrix around the nanostar, wherein the matrix may comprise the drug itself.

Another object of the present disclosure comprises, consists of, or consists essentially of a method of treating undesirable cells in a subject comprising: administering to the subject nanostar particles and a thermally-activated drug and a photo-activated drug; and irradiating the nanostar whereby the nanostar emits a thermal response and a photo response which activate the thermally-activated drug and the photo-activated drug.

Another object of the present disclosure comprises, consists of, or consists essentially of a method of treating undesirable cells in a subject comprising: administering to the subject nanostar particles whereby irradiation of the nanostar particles results in observable emission by the nanostar particles.

Another object of the present disclosure comprises, consists of, or consists essentially of a method of treating undesirable cells in a subject comprising: administering to the subject nanostar particles and a photo-activated drug; and irradiating the nanostar whereby the nanstar emits a photo-response such that both the photo-activated drug is activated and a detectable electromagnetic signal is emitted.

Another object of the present disclosure comprises, consists of, or consists essentially of a method of both detecting and treating undesirable cells in a subject comprising: administering to the subject nanostar particles and a thermally-activated drug; and irradiating the nanostar whereby the nanstar emits a thermal response and a photo-response such that both the photo-activated drug is activated and a detectable electromagnetic signal is emitted.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter.

Example 1

Polymer-Free Synthesis Method for Preparation of High-Yield Monodisperse Gold Nanostars TAT gold nanostars preparation. All chemicals were purchased from Sigma-Aldrich (St. Louis, Mo.) and used as received unless noted otherwise. Citrate gold seeds were prepared by adding 15 ml of 1% trisodium citrate to 100 ml of boiling $HAuCl_4$ (1 mM) under vigorous stirring for 15 minutes. The solution was cooled and filtered by 0.22 µpi nitrocellulose membrane. Gold nanostars (~60 nm diameter) were prepared using a seed-mediated method by quickly mixing $AgNO_3$ (100 µl, 3 mM) and ascorbic acid (50 µl, 0.1 M) together into 10 ml of $HAuCl_4$ (0.25 mM) with 12 nm citrate seeds (100 µl, $OD_{520}$: 3.1) followed by filtration using 0.22 µm nitrocellulose membrane.

Figure 9:
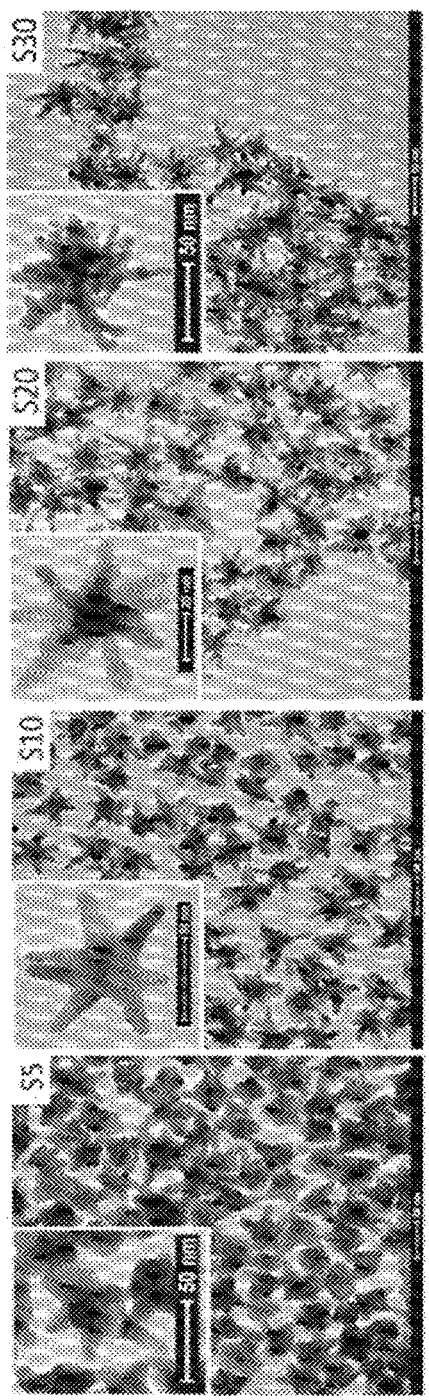
FIG. 9 is a series of TEM images of nanostars formed under different Ag$^+$ concentrations (S5: 5 µM, S10: 10 µM, S20: 20 µM, S30: 30 µM) according to one or more embodiments of the present disclosure.

In order to obtain nanostars of different geometry while keeping the particle size in a similar range, multiple factors were investigated, including pH, vortexing speed, and concentration of silver nitrate ($AgNO_3$), AA, $HAuCl_4$ and seed. In general, nanostars formed the most red-shift plasmon under lower pH, higher vortexing speed, and $AA/HAuCl_4$ ratio of about 1.5 to about 2. The concentration of the $HAuCl_4$ and the seeds can be selected so the resulting nanostars sizes were around 60 nm. Importantly, silver ions play a major role in controlling the formation of the star geometry. Without adding $Ag^+$ during synthesis, the resulting particles were polydisperse in both size and shape. The addition of a small amount of $Ag^+$ led to high-yield monodisperse star-shape particles. The overall particles diameters synthesized under different $Ag^+$ concentrations were within about 50 to about 70 nm. Under higher $Ag^+$ concentration, sharper and more numerous branches were formed, observable in the TEMs (see FIG. 9). The major role of $Ag^+$ is not to form Ag branches but to assist the anisotropic growth of Au branches on multi-twinned citrate seeds, but not single crystalline CTAB seeds, through several possible mechanisms that have been reported for the formation of nanorods, bipyramids and nanostars.[20]

Deep-tissue excitation and plasmon tunability of gold nanostars. It is efficient to excite in the NIR (700-900 nm) for deep tissue penetration of the excitation light. Plasmon tunability of the gold nanostars was achieved by adjusting the $Ag^+$ concentration as described herein above. Specifically, higher concentrations of $Ag^+$ progressively red-shifted the plasmon band. Higher $Ag^+$ concentrations lead to the formation of longer, sharper, and more numerous branches. A $Ag^+$ concentration of 5 µM resulted in a few protrusions, while a $Ag^+$ concentration of 30 µM resulted in multiple long, sharp branches appearing to branch even further (see FIG. 9). The overall size of the nanostars was calculated to be less than 100 nm, which is smaller than previously reported nanostars. It was determined that the plasmon peak of the nanostars was tunable from 600 nm to 1000 nm by adjusting the $Ag^+$ concentration (data not shown). The shift was accompanied by a visible change in the solution color from dark blue to dark grey as the plasmon red-shifted and broadened. Both the plasmon peak position and spectral width (as defined by the full width at half maximum (FWHM) of the plasmon peak) followed a linear trend with increasing $Ag^+$ concentration. A plateau was reached around an $Ag^+$ concentration of 30 µM in this study (data not shown). The nanostars can therefore be synthesized in a controlled fashion and can be useful for NIR applications.

Example 2

Enhanced Intracellular Delivery of the TAT-Functionalized Gold Nanostars and Efficient NIR Photothermolysis Using Ultralow Irradiance Previously published gold nanoparticles have great potential for plasmonic photothermal therapy (photothermolysis). However, their intracellular delivery and photothermolysis efficiency have yet been optimized. To achieve successful selective photothermolysis, nanostars need to be delivered sufficiently to the designated target cells without compromising cells' viability. It requires overcoming several biological harriers. Particles need to be physiologically stable, bind to the cell surface, and traverse the plasma membrane. In this experiment, TAT functionalization of a nanostar of the present disclosure is demonstrated to enhance intracellular delivery. In addition, efficient photothermolysis or photo therapy was achieved with lower irradiance.

The experiment described below shows that TAT-peptide functionalized gold nanostars entered cells significantly more than bare or PEGylated nanostars. Without being limited to any mechanism, it appeared that the major cellular uptake mechanism involves actin-driven lipid raft-mediated macropinocytosis, where particles primarily accumulate in macropinosomes but may also leak out into the cytoplasm. Following a 4-hour incubation of TAT-nanostars on BT549 breast cancer cells, photothermolysis was accomplished using 850 nm pulsed laser under an irradiance of 0.2 W/cm2, which is lower than the maximal permissible exposure of skin. The enhanced intracellular delivery and efficient photothermolysis demonstrated for the TAT-nanostars indicates their usefulness as an agent in cancer therapy.

Experimental Details

TAT gold nanostars preparation. All chemicals were purchased from Sigma-Aldrich (St. Louis, Mo.) and used as received unless noted otherwise. Citrate gold seeds were prepared by adding 15 ml of 1% trisodium citrate to 100 ml of boiling $HAuCl_4$ (1 mM) under vigorous stirring for 15 minutes. The solution was cooled and filtered by 0.22 µm nitrocellulose membrane. Gold nanostars (~60 nm diameter) were prepared using a seed-mediated method by quickly mixing $AgNO_3$ (100 µl, 3 mM) and ascorbic acid (50 µl, 0.1 M) together into 10 ml of $HAuCl_4$ (0.25 mM) with 12 nm citrate seeds (100 $OD_{520}$: 3.1) followed by filtration using 0.22 µm nitrocellulose membrane.[19] PEGylated gold nanostars were prepared by adding final 5 µM of $SHPEG_{5000}$ (O-[2-(3-mercaptopropionylamino)ethyl]-O'-methylpolyethylene glycol, MW 5000) to freshly synthesized gold nanostars for 10 minutes followed by one centrifugal wash then resuspending in pure ethanol. TAT-nanostars were prepared by mixing final 100 µM of TAT-peptide (residues 49-57, sequence Arg-Lys-Lys-Arg-Arg-Arg-Gln-Arg-Cys-CONH2 (SEQ ID NO: 1), SynBioSci, Livermore, Calif.) in 1 nM of PEGylated nanostars for 48 hours followed by two centrifugal washes in ethanol. The particles' hydrodynamic radius, ξ-potential and concentration were assessed by nanoparticle tracking analysis (NTA 2.2, Build 0337, NanoSight NS500; Nanosight Ltd. UK).

Cell Preparation and Imaging

The SKBR3 and BT549 breast cancer cells were cultured in McCoy 5A and RPMI-1640 growth media (10% fetal bovine serum (FBS); Invitrogen, Carlsbad, Calif.), respectively, in an incubator with a humidified atmosphere (5% $CO_2$) according to the ATCC's protocol. Cells in exponential growth phase were used in experiments. The cells were seeded onto 35 mm petri dishes for more than 2 days until ~80-90% confluency. To assess particle uptake, cells were fixed in 4% paraformaldehyde, stained with Hoescht 33342 (nuclear stain, 2 µg/ml in PBS; Invitrogen) and FM 1-43 FX (membrane stain, 4 µg/ml in PBS; Invitrogen) 30 min prior to imaging, then imaged under multiphoton microscopy (Olympus FV1000, Olympus America, Center Valley, Pa.). Real-time live cell imaging was done on a heating stage (37° C.) under the same multiphoton microscope. For TEM imaging, fixed cells were stained with $OsO_4$ and uranyl acetate followed by ethanol series dehydration and resin fixation. Ultrathin sections (~70 nm) were cut by an ultramicrotome, mounted on copper grids, stained with uranyl acetate/lead citrate, and imaged using a Fei Tecnai $G^2$ Twin at 80 kV.

Uptake Pathways Assessment

The particle cellular uptake pathways were assessed by using several uptake inhibitors: nocodazole (10 µg/ml; microtubule disruption), cytochalasin D (10 µg/ml; inhibits F-actin polymerization), chlorpromazine (10 µg/ml; inhibits clathrin-mediated endocytosis), genistein (10 µg/ml; inhibits caveolae-mediated endocytosis), methyl-β-cyclodextran (5 µg/ml; inhibits lipid raft), amiloride (100 µM; lowering submembraneous pH), and 4° C. (inhibits energy dependent endocytosis). Each cell sample was incubated 30 minutes with different inhibitors (in growth media). The old media was then replaced by new media containing both TAT-nanostars (0.1 nM) and the same inhibition condition for another hour. Except the cell sample receiving 4° C. treatment, all other samples were placed in the 37° C. incubator during the inhibition. Cell sample receiving no inhibition treatment was used as the control.

Uptake Time Series Assessment and Cytotoxicity Assay

TAT-nanostars (0.1 nM) were incubated 10 minutes to 24 hours with cell samples followed by two PBS washes and fixation. TPL imaging was performed as described above. The cytotoxicity from TAT-nanostars were examined by Resazurin-based toxicology assay (TOX8). Cells (3000 cells per well) were seeded on 96-well plates for two days prior to the particle treatment. After the TAT-nanostars incubation, each well was washed twice with PBS followed by replacement of fresh media. Resazurin (10% v/v) was added and the plate was kept in the incubator for another 1-2 hours. Resazurin (blue, nonfluorescent) is reduced by live cells to resafurin (pink, fluorescent). The fluorescence intensity was measured by a plate reader (FLUOstar Omega, BMG LABTECH GmbH, Germany).

Photothermal Therapy Assessment

For photothermal response validation, cells samples were incubated 4 hours with TAT-nanostars (0.1 nM) in growth media, and washed twice in PBS. During the photothermal treatment, cells samples were kept on a 37° C. heating stage and exposed to 850 nm pulsed laser irradiation (0.5-1 mW, 140 fs, 80 MHz). The laser power was measured with a thermopile detector. The treatment was performed by scanning the area (spot size 500×500 µm², 0.429 sec per scan) continuously for 3 minutes. Samples receiving media alone but the same laser irradiation were used as controls. After 0.5-1 hour, cells were examined by a live-cell staining procedure using fluorescein diacetate (FDA; 1 µg/ml in PBS) and propidium iodide (PI; 50 µg/ml in PBS) under a fluorescence microscope. Non-fluorescent FDA is converted to green fluorescent fluorescein by esterases in living cells. Membrane impermeant PI enters dead cells and displayed enhanced red fluorescence when hinds to DNA/RNA.

The TAT-NS were synthesized as illustrated in FIG. 1. To fabricate stable TAT-NS that resist aggregation in physiological environment and multiple washing cycles, cysteine-terminated TAT peptide (cTAT) and thiolated polyethylene glycol (SHPEG) were both used. Specifically, TAT-functionalized nanostars (TAT-NS) were synthesized by adding cysteine-terminated TAT peptide (cTAT) onto PEGylated nanostars (PEG-NS). Without the use of multi-step conjugation process, the method is extremely simple. In an attempt to utilize previous methods using pentapeptide CALNN or tiopronin to attach the TAT peptide to the NS,[39,40] the NS aggregated during the process. Because the 60 nm NS of the present disclosure is larger than previously studied AuNPs (14 nm for CALNN, 5 nm for tiopronin), it was hypothesized that these two chemicals might not be enough to stabilize the NS. Thus, a reverse sequence was investigated.[21] Specifically, adding cTAT into PEGylated NS (PEG-NS), resulted in stable TAT-NS. The ξ-potential increased from −25.5 mV (PEG-NS) to −17.6 mV (TAT-NS). In the case of the method described herein, cTAT may gradually penetrate the PEG layer and anchor onto the gold surface via the dative bond. Thus, the TAT functionality could be added without significantly disrupting the NP stability.

Using a fluorophore as a model to examine the surface binding, a consistent surface-enhanced Raman scattering (SERS) signal was observed from the fluorophore but decreasing fluorescence signal after each wash (data not shown); this indicated the presence of the fluorophore on the metal surface but much less in the PEG layer. Cellular uptake experiments revealed the heightened intracellular delivery of TAT-NS (data not shown), which confirmed the presence of TAT on nanostars.

Figure 10:
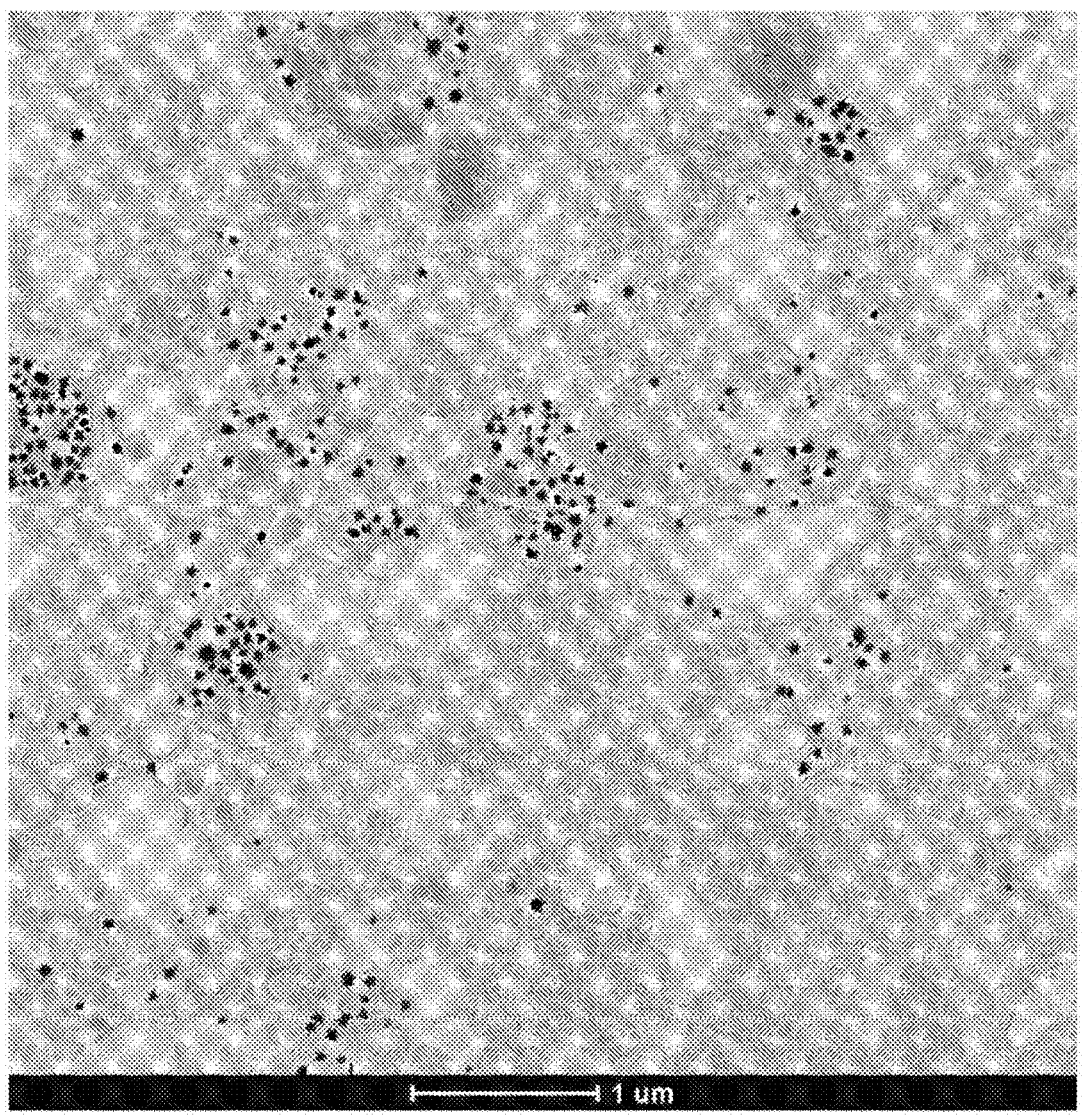
FIG. 10 is a TEM image of TAT-NS incubated in BT549 cells for 24 hours according to one or more embodiments of the present disclosure. While the majority of TAT-NS are observable inside the vesicles, a small amount of TAT-NS can be seen to have leaked out of the vesicles.

Experiments were performed showing enhanced intracellular delivery of TAT-NS in comparison to NS that had not been functionalized with TAT further confirming the presence of TAT on NS. The enhanced intracellular delivery of TAT-NS was easily visualized under TPL microscopy with high spatial resolution (data not shown). The cellular uptake of TAT-NS may differ between cell lines.[22] The BT549 breast cancer cell line was used here as a model to demonstrate the enhanced particle delivery. The intracellular distribution of TAT-NS, PEG-NS, and bare-NS was investigated and compared on both transmission electron microscopy (TEM) and TPL imaging. FIG. 10 shows a TEM image of TAT-NS incubated with BT549 cells for 24 hours. While the majority of TAT-NS are observable inside the vesicles, a small amount of TAT-NS can be seen to have leaked out of the vesicles. On TEM images, numerous TAT-NS are either accumulated in vesicles or scattered in the cytoplasm. This corresponded to the diffuse white pattern that was observed on the TPL image. Because the two-photon axial point-spread-function for a 20× water objective is around 1.7 μm,[47] each TPL image may constitute an optical thickness of more than 20 ultratome thin sections (~70 nm). For example, 100 NS observed on a TEM image correlates to ~2000 NS on a TPL image. This could explain why TAT-NS appeared nearly "saturated" inside cells on TPL image. Meanwhile, TAT-NS were observed in the nuclear region on TPL imaging. However, upon examining several cells on TEM, true intranuclear TAT-NS were not found, except some particles in the nuclear cleft, which still appeared to be in the cytoplasm. This result is in agreement with recent studies showing intranuclear localization of smaller TAT-functionalized nanoparticles of 50 nm or less.[45, 46, 48, 49] The mismatch between TPL and TEM images suggests that intracellular particle distribution characterization using optical methods should be confirmed by TEM. In agreement with previous studies,[16, 32] PEGylation only resulted in minimal cellular uptake at this particle concentration. In addition, it was observed that hare NS without any protective layer tend to aggregate in the vesicles, forming large dense spots on TEM image, corresponding to big white punctates on TPL images. Comparing these 3 surface modifications (TAT, PEG, bare), TAT functionalization greatly facilitates the uptake of gold nanostars. In the following paragraphs, the uptake mechanism, temporal profile, and cytotoxicity is addressed.

TAT peptide operates by anchoring on the plasma membrane and translocating primarily via macropinocytosis, which refers to the formation of large endocytic vesicles of irregular sizes and shapes, generated by actin-driven invagination of the plasma membrane.[31] It's been shown that TAT peptide, through multidentate hydrogen binding from arginines (not lysines) with the anionic groups on the membrane (e.g. heparan sulfate proteoglycans, filamentous actin), generates membrane deformation and cytoskeleton reorganization (e.g. actin ruffling) to translocate either directly through membrane or endocytosis.[50] TAT functionalized proteins or quantum dots also enter cells via macropinocytosis.[40, 41] However, this process has yet to be properly characterized on TAT functionalized gold nanoparticles. Both TEM and TPL imaging were applied to assess TAT-NS' intracellular trafficking pathway.

The TAT-NS cellular uptake pathway was assessed using TPL and TEM images. TAT-NS was incubated with BT549 cells for 1 hour under 37° C. without inhibitors and images were generated. The TEM images showed TAT-NS in vesicles, in cytoplasm, on membrane, and upon invagination. In addition, TAT-NS treated cells were incubated with different inhibitors and TLP and TEM images were obtained. The TLP images showed that cellular uptake of TAT-NS was inhibited by 4° C., cytochalasin D, methyl-β-cyclodextrin, and amiloride but not chlorpromazine and genistein. TEM images showed that numerous TAT-NS are seen bound to the membrane. The binding was not homogeneous throughout the membrane, but formed a patchy distribution; possibly as a result of heterogeneous distribution of heparan sulfate proteoglycans associated with lipid rafts. The images also showed the surface ruffling in the process of forming a large macropinosome to take up TAT-NS. The ruffling is a common behavior in macropinocytosis that is induced upon stimulation.[31] In addition, the vesicle sizes of around 500 nm were observed, which is greater than a typical vesicle size for clathrin-mediated (100-150 nm) or caveola-mediated (50-60 nm) endocytosis. In agreement with Kreptic et al. and Berry et al., some particles could be observed outside the vesicles in the cytoplasm;[45, 46] this may reflect particles leaking out from macropinosomes into the cytoplasm. All these structural features are in concordance to the behavior of macropinocytosis.

To further assess the TAT-NS internalization pathway, cells were pretreated with several inhibitors for 30 min, incubated with TAT-NS for an hour, then examined under TPL microscopy (data not shown) following a previous protocol.[51, 52] It was found that the TAT-NS internalization was inhibited by 4° C. (energy blockade), amiloride (AMR; lowering submembraneous pH), cytochalasin D (cytoD; F-actin inhibition), and methyl-β-cyclodextrin (MβCD; lipid raft inhibition), but not chlorpromazine (CPM; clathrin inhibition), genistein (GNT; caveola inhibition) and nocodazole (NCZ; microtubule disruption; data not shown). This confirms that the TAT-NS internalization is an energy dependent, actin-driven, and lipid raft mediated macropinocytosis, which is in agreement with the findings from Wadia et al. and Ruan et al. on TAT-protein and TAT-QD, respectively.[40, 41] The clathrin or caveola, although previously were reported on TAT facilitated uptake,[30] may play a less significant role in this cell type. TAT-NS adhesion to the plasma membrane and actin ruffles, however, were not inhibited because the multidentate hydrogen binding is not affected by the inhibitors. Based on the TEM/TPL results and inhibitor studies, it appears that the primary TAT-NS uptake pathway is through actin-driven and lipid raft-mediated macropinocytosis.

Before a photothermolysis study was performed, it was desired to ensure a sufficient intracellular TAT-NS delivery without compromising cell viability. Thus, the temporal uptake profiles were examined along with the cytotoxicity assay. A time-dependent uptake of TAT-NS on BT549 cells experiment was performed and TLP and TEM images were obtained (data not shown). In 10 min, TAT-NS started anchoring onto the plasma membrane. Real-time live cell TPL imaging confirmed the surface binding by showing single free-moving TAT-NS adhering inhomogeneously to the surface membrane. Within an hour, intracellular uptake could be seen, forming larger-sized punctates on TPL images. These large bright punctates, with sizes around 1 μm on TPL microscopy, were most likely macropinosomes. Smaller and dimmer punctates might be smaller vesicles or even single NS. Later, TAT-NS accumulated towards the perinuclear region and eventually "saturated" the cytoplasm with numerous large bright punctates at 24 hours. Incubation of TAT-NS for 72 hours showed similar particle density as in 24 hours (data not shown). Under TEM, these large bright punctates on TPL imaging were seen to be mostly TAT-NS accumulated in vesicles. Krpetic et al. also observed particles accumulation mostly in the vesicles at 24 hours, but particles were cleared after replacing the growth medium.[45] The fate of TAT-NS after 24 hours was not examined in this study.

The time series TPL images of cells treated with TAT-NS showed incremental accumulation. The cellular metabolic activity became affected by TAT-NS after 24-hour incubation (data not shown). Such effects depended on both the coating type (bare, PEG, TAT) and particle concentration. At 8-hour incubation, the cell viability was not significantly different from the control (0 hr), however the statistical distribution of viability was wide. Although a higher particle density under longer incubation is desired for higher photothermolysis efficiency, to reduce the confounding effect from altered cell viability 4-hour TAT-NS incubation was chosen for the photothermolysis study.

The photothermolysis was performed on the same multiphoton microscope with raster scanning for 3 minutes (data not shown). The average irradiance (i.e. the power density) was controlled by the acoustic-optic modulator and the scanning area from the microscope's software. Here, at 1 mW (12.5 pJ per pulse; irradiance: 0.4 W/cm$^2$), no laser-induced damage was seen on cells treated 4h with media only or PEG-NS. Irradiating cells immersed with PEG-NS (0.1 nM) also did not produce damage (data not shown), most likely because the free-floating PEG-NS were not concentrated enough in cells. In contrast, a distinct square of ablation (empty area) was observed when irradiating (0.4 W/cm$^2$) cells incubated 4 hours with TAT-NS. Real-time live cell TPL imaging showed cells shrinking or moving outwards upon irradiation. At 0.5 mW (6.25 pJ per pulse; irradiance: 0.2 W/cm$^2$), a large portion of cells were damaged but still attached on the dish. Such irradiance (0.2 W/cm$^2$) is not only lower than previously reported values using a pulsed laser,[23, 28] but also lower than the MPE of skin to laser irradiation (0.4 W/cm$^2$ at 850 nm) by ANSI regulation.[26] This is the first demonstration of cellular photothermal therapy at such a low irradiance. With more NS inside cells, the required irradiance could be even lower. Combination of pulsed laser irradiation and enhanced intracellular delivery of TAT-NS clearly can bring forth a very efficient photothermolysis system.

These results demonstrate an efficient photothermolysis at an ultralow irradiance (0.2 W/cm$^2$), which is the lowest value ever reported. The enhanced intracellular delivery of TAT-NS substantially potentiates the photothermolysis efficiency without compromising cell viability. The photothermolysis process is for the first time recorded on live cells. The traceability of NS under multiphoton microscopy greatly simplifies both the study of particle's intracellular trafficking and the monitoring of photothermolysis process on live cells. Since multiphoton microscopes utilize tissue penetrating NIR laser, a potential for photothermolysis on deep-seated tumors is possible. Combining NS and TPL microscopy also makes it possible for mechanistic understanding on particle's kinetic behavior. TAT-NS uptake examined on both TEM and multiphoton microscopy confirms that their uptake mechanism involves primarily actin-driven lipid raft-mediated macropinocytosis. These results indicate the nanostars of the present disclosure functionalized with a cell penetrating peptide or other bioreceptor targeted delivery of cargo to selected tissues such as tumors. Thus, the gold nanostars can be useful as a therapeutic and diagnostic agent in cancer therapy.

Example 3

Demonstration of Cell-Killing Effect of Psoralen-TAT-Nanostar Drug Under Two-Photon Excitation TAT and PsTAT functionalized gold nanostars preparation. All chemicals were purchased from Sigma-Aldrich (St. Louis, Mo.) and used as received unless noted otherwise. Gold nanostars (60 nm diameter) were prepared using a seed-mediated method by quickly mixing AgNO$_3$ and ascorbic acid together into 10 ml HAuCl$_4$ (0.25 mM) with 12 nm citrate seeds (OD$_{520}$: 2.8). PEGylated gold nanostars were prepared by adding final 5 μM of SHPEG$_{5000}$ (O-[2-(3-Mercaptopropionylamino)ethyl]-O'-methylpolyethylene glycol, MW 5000) to freshly synthesized gold nanostars for 10 minutes followed by one centrifugal wash then resuspension in pure ethanol. TAT-nanostars were prepared by mixing final 100 μM of TAT-peptide (residues 49-57, sequence Arg-Lys-Lys-Arg-Arg-Arg-Gln-Arg-Cys-CONH2, SynBioSci, Livermore, Calif.) in 1 nM of PEGylated nanostars for 48 hours followed by two centrifugal washes. PsTAT-nanostars were prepared by mixing final 100 μM of PsTAT-peptide (psoralen-Arg-Lys-Lys-Arg-Arg-Arg-Gln-Arg-Arg-Cys-CONH$_2$ (SEQ ID NO: 1) RS Synthesis LLC, Lexington, Ky.) in 1 nM of PEGylated nanostars for 48 hours followed by two centrifugal washes.

Cell preparation and imaging. The SKBR3 and BT549 breast cancer cells were cultured in McCoy 5A and RPMI-1640 growth media (10% fetal bovine serum (FBS); Invitrogen, Carlsbad, Calif.), respectively, in an incubator with a humidified atmosphere (5% CO$_2$) according to the ATCC's protocol. Cells in exponential growth phase were used in experiments. The cells were seeded onto 35 mm petri dishes for more than 2 days until ~80-90% confluency. To assess particle uptake, cells were fixed in 4% paraformaldehyde, stained with Hoescht 33342 (nuclear stain, 2 μg/ml in PBS; Invitrogen) 30 minutes prior to imaging, then imaged under multiphoton microscopy (Olympus FV1000, Olympus America, Center Valley, Pa.).

Uptake time series assessment and cytotoxicity assay. TAT-nanostars (0.1 nM) were incubated 10 minutes to 24 hours with cell samples followed by two PBS washes and fixation. TPL imaging was performed as described above. The cytotoxity from TAT-nanostars were examined by Resazurin-based toxicology assay (TOX8). Cells (3000 cells per well) were seeded on 96-well plates for two days prior to the particle treatment. After the TAT-nanostars incubation, each well was washed twice with PBS followed by replacement of fresh media. Resazurin (10% v/v) was added and the plate was kept in the incubator for another 1-2 hours. Resazurin (blue, nonfluorescent) is reduced by live cells to resafurin (pink, fluorescent). The fluorescence intensity was measured by a plate reader (FLUOstar Omega, BMG LABTECH GmbH, Germany).

Photothermolysis assessment. For photothermal response validation, cells samples were incubated 4 hours with TAT-nanostars (0.1 nM) in growth media, and washed twice in PBS. During the photothermal treatment, cells samples were kept on a 37° C. heating stage and exposed to 850 nm pulsed laser irradiation (0.5-1 mW, 140 fs, 80 MHz). The treatment was performed by scanning (spot size 500×500 μm$^2$, 0.429 sec per scan) continuously for 3 minutes. Samples receiving media alone but the same laser irradiation were used as controls. After 1 hour, cells were examined by a live-cell staining procedure using fluorescein diacetate (FDA; 1 μg/ml in PBS) and propidium iodide (PI; 50 μg/ml in PBS)

under a fluorescence microscope. Non-fluorescent FDA is converted to green fluorescent fluorescein by esterases in living cells. Membrane impermeant PI enters dead cells and displayed enhanced red fluorescence when binds to DNA/RNA.

Demonstration of Cell-Killing Effect of Psoralen-TAT-Nanostar Drug under Two-photon Excitation. Nanostars show broad emission under two-photon excitation. This emission was harnessed for the activation of psoralen in vitro. Cells were incubated with nanostar solutions for 4 hr. The TAT peptide was used to enhance particle uptake. After incubation the cells were washed twice in PBS and fresh media was added. Three-minute exposures of laser radiation under a two-photon microscope were used. Cell viability was assessed with FDA/PI staining.

When a low-power laser (0.4 mW) was used, it was observed that there was cell killing with the psoralen containing S30 nanostar particles (S30-PsTAT) but little to none with nanostar particles with just TAT (S30-TAT) (data not shown). This study indicated that S30 nanostar particles containing psoralen (S30-PsTAT) exhibit cell killing effect under 2-photon excitation under low laser power excitation.

The power of the laser was increased to 1 mW to further investigate the effect on cells. The psoralen containing S30 nanostar particles (S30-PsTAT) showed an enhanced killing effect compared to the nanostar particles with just TAT (S30-TAT), at both 850 nm and 740 nm two-photon laser excitation (data not shown). Since a cell killing effect was observed for nanostar particles with just TAT (S30-TAT), this effect can be attributed to a therapeutic activity (e.g., thermolysis, ROS generation) different from psoralen. Thus the results with psoralen-containing S30 nanostar particles (S30-PsTAT) can be attributed to a combined multi-modality therapeutic effect of the drug.

Example 4

Cell-Penetrating Peptide Enhanced Intracellular Raman Imaging and Photodynamic Therapy The combination of therapeutic and diagnostic components into a single construct, i.e. theranostics, is an emerging field of medical research that aims at further improving personalized medicine.[65-69] Such composite materials allow for the imaging and detection of a specific target, monitoring biological and therapeutic processes, followed by localized release of therapeutic agents. In this way, theranostics can greatly improve the specificity and selectivity of various treatments, increasing efficacy while reducing unwanted side effects. The present inventor's laboratory has recently been involved in the development and application of a wide variety of plasmonic platforms ranging form nanoparticles to nanoposts, nanowires and nanochips for use as surface-enhanced Raman scattering (SERS).[70-73] Plasmonic nanoprobes have been developed for various photon-triggered therapeutics, including photothermal and photodynamic therapies.[19, 74-76]

Raman-labeled nanoparticle probes have gained increasing interest in bio-labeling applications due to their advantages over conventional fluorescence methods.[77-94] Fluorophores are highly susceptible to photobleaching, and solvent effects heavily influence fluorescence emission. Multiplex detection with fluorescence is also difficult because of the broad, featureless emission peaks, and the need for multiple specific excitation wavelengths. SERS spectra are generally unaffected by photobleaching and solvent or environmental effects. The potential for multiplexing is greater with Raman spectra, owing to the narrow fingerprint-like peaks and the need for only one excitation source. The use of a Raman label whose absorption band overlaps with the laser excitation line can provide surface-enhanced resonance Raman scattering (SERRS), further increasing the signal by a few orders of magnitude.

Photodynamic therapy (PDT) is a modality for the treatment of a number of diseases, including cancer. PDT involves the generation of reactive oxygen species (ROS) by a photosensitizer molecule when excited by the appropriate wavelength of light.[95] The generated ROS then reacts with nearby cellular components causing cell death by apoptosis or necrosis.[96] Protoporphyrin IX (PpIX) is a well-known photosensitizer drug for PDT; however, it has limited efficacy when applied directly to the target site due to its aggregation and poor solubility in aqueous environments.[97-98] Mesoporous silica nanoparticles have been shown to be highly effective at encapsulating various PDT drugs while still maintaining their efficacy.[96-97, 99-103] This can be achieved due to the fact that the drug does not have to be released at the target; diffusion of molecular oxygen to the drug, and diffusion of the generated reactive oxygen species to the environment around the nanoparticle are adequate for therapeutic effects. Silica nanoparticles have also been used as a delivery vehicle for hydrophobic anticancer drugs.[104] Gold nanostars are a useful nanoplatform for SERS diagnostics since they exhibit tunable plasmon bands in the NIR tissue optical window and have multiple sharp branches acting as "hot-spots" for the SERS effect.[76, 105]

A theranostic system combining Raman detection and photodynamic therapy (PDT) is presented below. The theranostic nanoplatform was created by loading the photosensitizer, Protoporphyrin IX, onto a Raman-labeled gold nanostar. A cell-penetrating peptide, TAT, was used to enhance intracellular accumulation of the nanoparticles in order to improve their efficacy. The plasmonic gold nanostar platform was designed to increase the Raman signal via the surface-enhanced resonance Raman scattering (SERRS) effect. Theranostic SERS imaging and photodynamic therapy using this construct were demonstrated on BT-549 breast cancer cells. In the absence of the TAT peptide, nanoparticle accumulation in the cells was not sufficient to be observed by Raman imaging, or to produce any photosensitization effect after a 1-hour incubation period. There was no cytotoxic effect observed after nanoparticle incubation, prior to light-activation of the photosensitizes.

Experimental

Materials: Gold(III) chloride trihydrate (HAuCl$_4$.3H$_2$O), trisodium citrate dihydrate (C$_6$H$_5$O$_7$Na$_3$.2H$_2$O), 1N HCl, L(+)-ascorbic acid (AA), tetraethyl orthosilicate (TEOS), O-[2-(3-Mercaptopropionylamino)ethyl]-O'-methylpolyethylene glycol (mPEG-SH, MW 5 k), Protoporphyrin IX (PpIX), 3,3'-Diethylthiadicarbocyanine iodide (DTDC), fluorescein diacetate (FDA), propidium iodide (PI), and Resazurin based Toxicology Assay Kit (TOX8) were purchased from Sigma-Aldrich (St. Louis, Mo., USA) at the highest purity grade available. Silver nitrate (AgNO$_3$, 99.995%) was supplied by Alfa Aesar (Ward Hill, Mass., USA). Pure-grade ethanol and ammonium hydroxide (NH$_4$OH, 29.5%) were obtained through VWR (Radnor, Pa., USA). Ultrapure water (>18 MΩ cm$^{-1}$) was used in all preparations. All glassware was cleaned with aqua regia, washed with copious amounts of water, and dried prior to use. Cell culture media and supplements, ProLong Gold Antifade Reagent, and Hoescht 33342 were purchased from Invitrogen (Carlsbad, Calif.). TAT-peptide (residues 49-57, sequence Arg-Lys-Lys-Arg-Arg-Arg-Gln-Arg-Cys-CONH$_2$) (SEQ ID NO: 1) was ordered from SynBioSci (Livermore, Calif.).

Instrumentation: Raman spectra were recorded on a Renishaw inVia Raman microscope (Gloucestershire, UK), controlled by WiRE 2.0 software, using an 1800 g mm$^{-1}$ grating with 633 nm (8 mW) excitation. Fluorescence emission spectra were collected using an Edinburgh Photonics FLS920 fluorescence spectrometer (Livingston, UK). Transmission electron microscopy (TEM) was performed on a FEI Tecnai G$^2$ Twin transmission electron microscope (Hillsboro, Oreg., USA) with an accelerating voltage of 200 kV. Absorption spectra were acquired on a Shimadzu UV-3600 (Columbia, Md.). Particle concentrations and size distributions were measured by Nanoparticle Tracking Analysis (NTA) with a NanoSight NS500 (Amesbury, UK). The fluorescence intensity of the Resazurin-based toxicology assay was measured by a FLUOstar Omega plate reader (BMG LABTECH GmbH, Germany). Photodynamic therapy treatment and cell viability imaging were performed on a Zeiss Axiovert 200M inverted microscope (Thornwood, N.Y.) equipped with an X-Cite Series 120 mercury arc lamp (Lumen Dynamics, Mississauga, ON, Canada). Images were recorded with a Canon EOS Rebel XTi (Tokyo, Japan) mounted to the front port of the microscope. The TPL images were recorded using a commercial multiphoton microscope (Olympus FV1000, Olympus America, Center Valley, Pa.) with a femtosecond Ti:sapphire laser (Chameleon Vision II, Coherent, Santa Clara, Calif.) used for excitation.

Raman-Labeled Nanostar Synthesis: The nanostars were synthesized as described. A gold seed solution was prepared by bringing 100 mL of 1 mM HAuCl$_4$ to a rolling boil and adding 15 mL of 1% trisodium citrate under vigorous stirring. The solution was kept boiling for 15 minutes, cooled, filtered with a 0.22 µm nitrocellulose membrane, and stored at 4° C. Nanostars were grown from the seed by adding 100 µL of the gold seed to a solution containing 10 mL of 0.25 mM HAuCl$_4$ and 10 µL of 1N HCl, followed quickly by simultaneous addition of 100 µL 1 mM AgNO$_3$ and 50 µL 0.1 M AA under moderate stirring. Within 10 seconds the solution turned from light red to a deep blue. The stock concentration of nanoparticles was approximately 0.1 nM, as determined by Nanoparticle Tracking Analysis (NTA).

Freshly synthesized nanostars (10 mL) were conjugated with mPEG-SH (5 µM final concentration) under gentle stirring for 15 minutes. The PEGylated particles were then centrifuged (3.5 k rcf, 15 minutes) twice at 4° C. to remove excess PEG and redispersed in water. DTDC (0.2 µM final concentration) in ethanol was added to this solution and allowed to stir overnight. The DTDC-tagged particles were centrifuged (3.5 k rcf, 15 minutes) twice at 4° C. to remove excess DTDC and resuspended in water (AuNS-DTDC).

Encapsulation of Protoporphyrin IX and TAT Conjugation: A modified Stöber method was used for formation of the silica shell.[106] The labeled nanostar solution was centrifuged at 4° C. (3.5 k rcf, 15 minutes) and resuspended in 2 mL of ethanol. Under gentle stirring, the solution of nanostars was added to a 20 mL glass vial containing 2.0 mL of water and 7.0 mL ethanol. Protoporphyrin IX (1 µM final concentration) in ethanol and 180 µL of NH$_4$OH were added to the mixture. Silica coating was initiated by the addition of 30 µL 10% TEOS in ethanol, and the reaction was allowed to proceed for three hours. The nanoparticles were then centrifugally purified (3.5 k rcf, 15 minutes) two times and redispersed into 5 mL of ethanol. TAT conjugation was achieved by passive adsorption; a final concentration of 100 µm TAT was added to the ethanolic solution of particles and allowed to stir overnight.

Cell Culture and Nanoparticle Incubation: BT-549 breast cancer cells were cultured in modified RPMI 1640 medium (Gibco 22400-089) supplemented with 10% fetal bovine serum and 0.023 IU/mL insulin, and incubated at 37° C. in a humidified 5% CO$_2$ atmosphere. For PDT studies, cells were seeded into 6-well plates. Cells prepared for Raman mapping were grown on sterilized glass coverslips in 6-well plates. Cytotoxicity was assessed using cells grown in a 96-well plate. Cell samples for two-photon luminescence imaging were grown in 35 mm Petri dishes. All samples were grown to ~80% confluency before use.

The nanoparticle solution was prepared for cellular incubation by centrifugally washing once with water, then resuspending into complete growth medium to a particle concentration of 0.1 nM. Cells were incubated with the particle-containing medium for one hour. After incubation, the medium was aspirated and the cells were washed three times with PBS. For the cytotoxicity assay, growth medium was replaced and the cells were cultured for 24 hours. Resazurin (10% v/v) was added and the plate was kept in the incubator for 1 hour. Resazurin (blue, nonfluorescent) is reduced by live cells to resorufin (pink, fluorescent). The fluorescence intensity of resorufin was then measured by a plate reader. For two-photon luminescence imaging, cells were fixed in 4% paraformaldehyde and stained with Hoescht 33342 (2 µg mL$^{-1}$ in PBS) 30 minutes prior to imaging.

Raman Mapping: After particle incubation the cells were fixed with a 4% paraformaldehyde solution and rinsed with water to remove any remaining salt. The coverslips were removed from the 6-well plate and mounted onto glass slides following the protocol for the ProLong Gold Antifade Reagent. After curing for 24 hours, the edges of the coverslip were sealed with clear nail polish to extend the sample life. Raman mapping was performed on the Renishaw inVia Raman microscope. Cells were located under brightfield illumination with a 40× objective. Spectra were collected with the grating centered at 1100 cm$^{-1}$ (~600 cm$^{-1}$ bandwidth) during a 5-second data acquisition. The Raman image maps were created by collecting spectra at multiple points on a grid with 2-µm spacing over the 2D region of a cell. The baseline-subtracted intensity from the DTDC peak between 1120 and 1150 cm$^{-1}$ was integrated and then displayed over the grid using a color scale to depict the intensity variation across the area.

Photodynamic Therapy: After particle incubation, the cells were kept in PBS to prevent any optical interference from the phenol red in the cell culture medium. A region of cells was focused on using a 40× phase contrast objective, and then irradiated with light from the mercury arc lamp after passing through a DAPI filter (377/50 nm). The measured power density was 4.4 W/cm$^2$. After treatment, the PBS was replaced with growth medium and cells were cultured for 4 hours prior to viability staining. Cell viability was assessed by incubating cells for 5 minutes in a solution of PBS containing 1 µg mL$^{-1}$ FDA for live cells (green) and 50 µg mL$^{-1}$ PI for dead cells (red), and imaging on a fluorescence microscope.

Data Analysis: Smoothing and baseline subtraction of Raman spectra was performed in MATLAB R2012a. Spectra were smoothed using the 'smooth' function with parameters: span=15, method='sgolay', degree=2. The baseline was removed using a numerical algorithm developed in our laboratory, which uses a moving window to locally determine the background fluorescence. Unprocessed versions of the Raman spectra presented in the text can be found in the electronic supplementary information. Mathematica 8.0.4 was used to integrate the area under the curve for fluorescence spectra of PpIX. Scale bars were added to images using IMAGEJ 1.46j. All graphs were created in Microsoft Excel for Mac Version 14.2.3.

Figure 11:
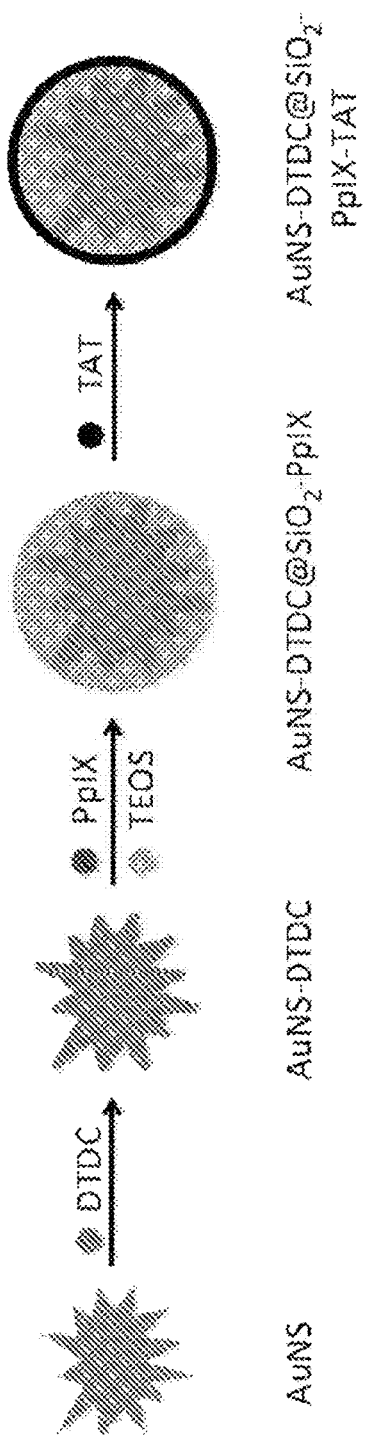
FIG. 11 is schematic depiction of a synthesis of gold nanostars having a Raman label, a photosensitize and a cell penetrating peptide according to one or more embodiments of the present disclosure.

FIG. 11 presents a visual overview of the steps required to prepare the theranostic nanoplatform. The Raman-labeled gold nanostars (AuNS) were prepared as described. PEGylated AuNS were allowed to stir overnight in a solution containing 0.2 µM of the dye DTDC. The sulfur groups of the thiacarbocyanine dye aid in adsorption to the gold surface.

Figure 12:
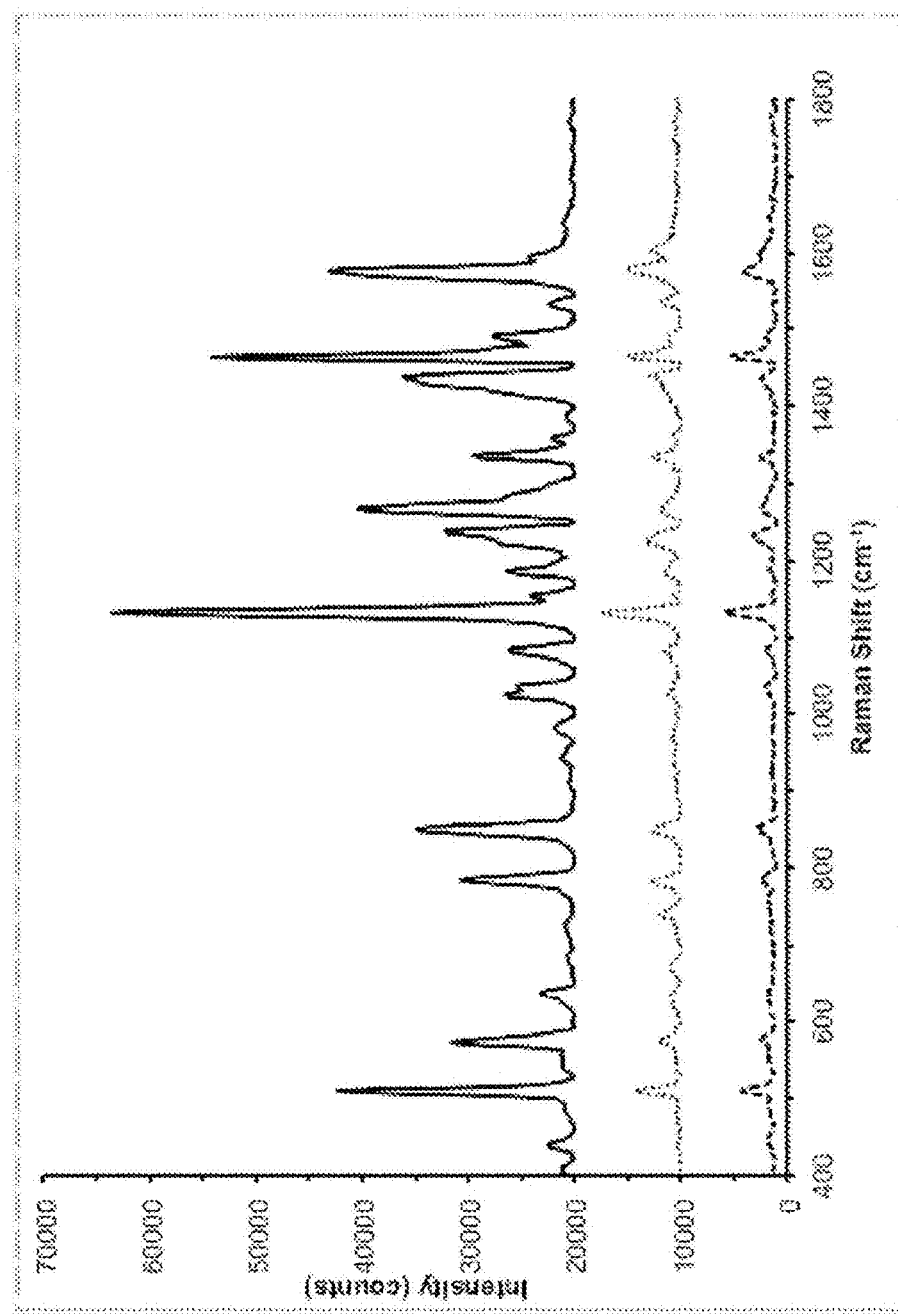
FIG. 12 is a SERRS spectra of a gold nanostar according to one or more embodiments of the present disclosure. AuNS-DTDC solution (solid, top), AuNS-DTDC@SiO2-PpIX-TAT solution (dotted, middle), and a point collection from a cell that had been incubated with AuNS-DTDC@SiO2-PpIX-TAT (dashed, bottom). All spectra were acquired at 633 nm excitation (8 mW) with a 10 second integration time. The solution spectra were recorded using a 10× objective with the particles suspended in water, while the intracellular Raman spectrum was recorded with a 40× objective. Spectra are baseline-subtracted and offset for clarity.

FIG. 12 shows the SERRS spectrum of the unwashed AuNS-DTDC particle solution before silica coating (solid line), indicating binding of the dye at or near the particle surface. The decrease in SERRS intensity after silica coating is likely due to displacement of any DTDC that was not bound directly to the particle surface by the condensation of silica onto the PEG layer.

Figure 13A:
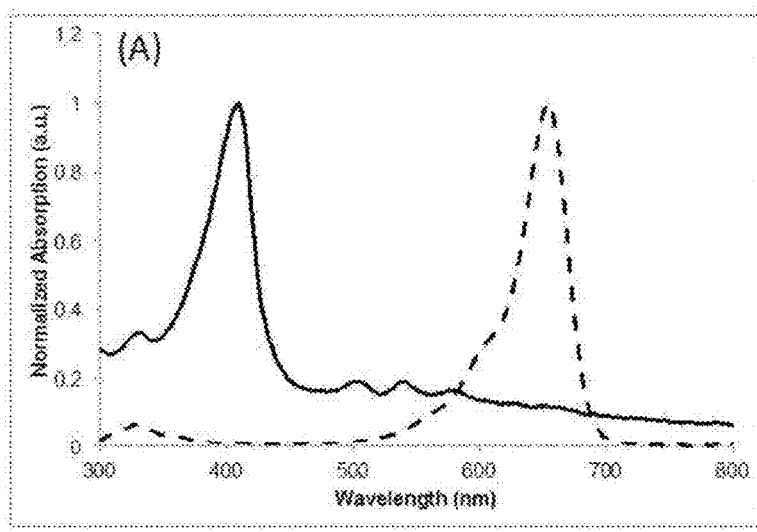
FIGS. 13A-13B are absorption spectra. A) Absorption spectra of free PpIX (solid) and DTDC (dashed) in ethanol. B) Absorption spectra of the AuNS-DTDC before (solid, left axis) and after (dotted, left axis) silica coating (particles dispersed in water) and fluorescence emission from the AuNS-DTDC@SiO2-PpIX-TAT (dispersed in ethanol) under 415 nm excitation (dashed, right axis) according to one or more embodiments of the present disclosure.
Figure 13B:
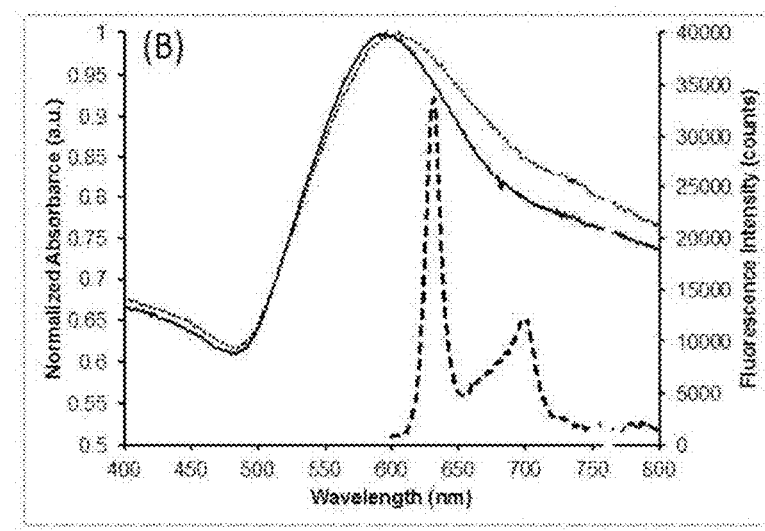

The PEGylated, labeled AuNS was coated with silica using a method described previously by Fernández-López et al.[106] Adding PEG to the AuNS enhances particle stability in ethanol so that a modified Stöber method can be used to form the silica shell. As seen in FIGS. 13A and 13B, there is a red shift in the extinction spectrum of the AuNS after silica coating. PpIX loading of the silica shell was achieved by adding 1 µM of the photosensitizer to the reaction mixture prior to initiation of silica condensation. The drug was sequestered in the pores of the silica matrix, and fluorescence emission of PpIX was observed from the synthesized particles after being washed (FIGS. 13A and 13B).

A calibration curve (data not shown) was established using the fluorescence emission of PpIX under 415-nm excitation and it was estimated that 0.37±0.03 µM of the initial 1 µM PpIX was encapsulated on the AuNS. The fluorescence intensity of PpIX remaining in solution after the silica coating was used to make this estimation. When using the fluorescence intensity from the particle solution itself, a loaded PpIX concentration of 0.18±0.03 µM is determined. This discrepancy is likely largely attributed to the inner filter effects of the nanostars, which have an optical density around 0.65 in the excitation band for PpIX and an average optical density of about 0.8 in the PpIX emission band.

The particle samples were also tested for any PpIX leaching due to plasmonic heating of the nanostars. A HeNe laser (633 nm) was chosen due to the close matching of the excitation wavelength with the maximum absorption of the nanostars. Aliquots of 100 µL of AuNS-DTDC@SiO$_2$-PpIX or AuNS-DTDC@SiO$_2$—PpIX-TAT were placed into a 96-well plate and irradiated with an 8 mW 633 nm laser for various amounts of time. The samples were spun down at 5 k ref, and PpIX fluorescence was measured from the supernatant. It was seen that after 15 minutes of irradiation, less than 25% of the PpIX had been leached from the nanoparticles (data not shown). The TAT-coated particles also showed a slightly lower rate of PpIX release, possibly due to partial blocking of the silica pores on the outer surface. It is worthy to note that when the delivered light flux is equal to that which is used for PDT (at 1.5 min irradiation time), only ~10% of the loaded PpIX had escaped from the silica shell.

TEM was used to characterize the particle size and morphology.

Figure 14:
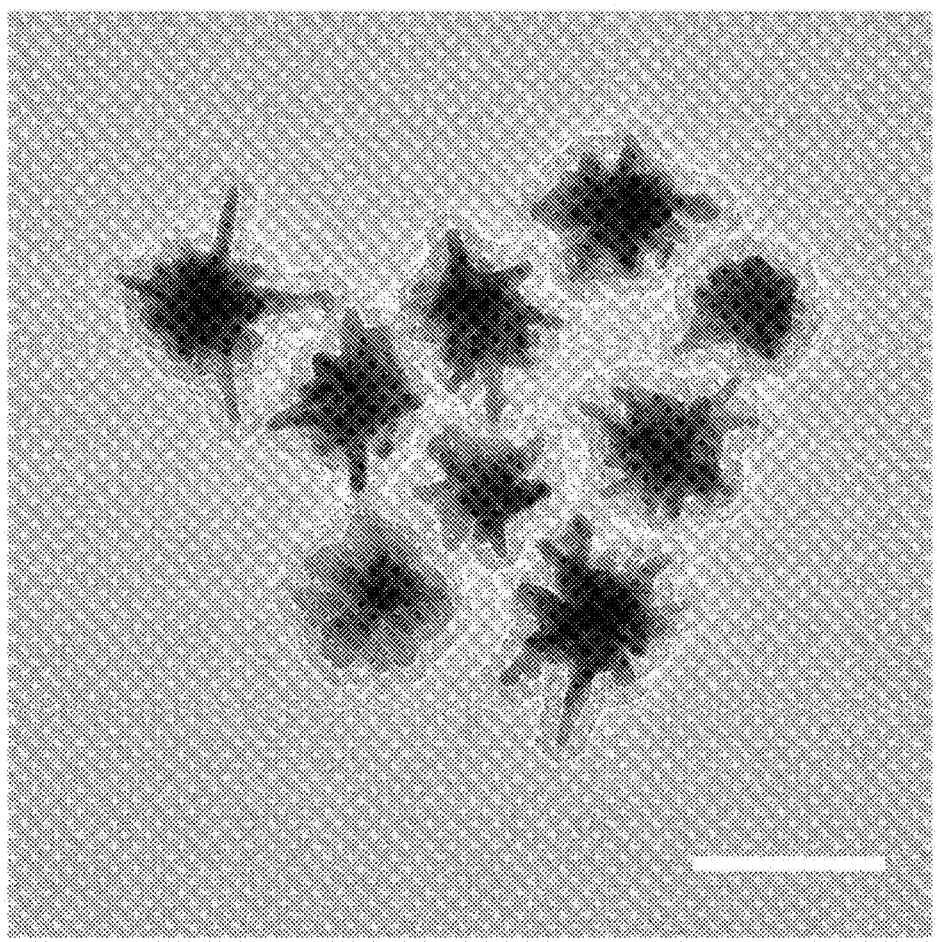
FIG. 14 is a TEM micrograph of the silica coated AuNS according to one or more embodiments of the present disclosure. The scale bar is 100 nm.

FIG. 14 shows that addition of PpIX did not impact formation of complete silica shells on the AuNS. The hydrodynamic size of the AuNS-DTDC@SiO$_2$—PpIX was measured to be 123±34 nm by Nanoparticle Tracking Analysis (data not shown). The final particle modification step was conjugation with the TAT peptide. Electrostatic interaction between the negatively charged silica-coated particles and the positively charged TAT peptide induce an effective attachment method. This attachment is confirmed by the dramatic increase in intracellular particle accumulation observed for the TAT functionalized particles by two-photon luminescence imaging (data not shown).

Although silica nanoparticles are generally considered to be non-toxic, the pronounced increase in particle uptake caused by the TAT peptide warranted the use of a cytotoxicity assay to measure the impact of this dense particle loading. Cells in a 96-well plate were incubated with various particle samples at a concentration of 0.1 nM for 1 hour, washed in PBS, and then cultured for 24 hours. After this time period, a Resazurin assay was used to assess the cytotoxicity of each particle sample (data not shown). Each data set is the average fluorescence intensity from a column on the 96-well plate (8 measurements). There was no statistically significant observable difference in cell viability for any of the particle-incubated samples compared to the control sample.

Raman images were created by taking a 5-second spectral acquisition centered at 1100 cm$^{-1}$ (~600 cm$^{-1}$ bandwidth) at each point on a grid with 2-µm spacing over the 2D area of a cell. The integrated DTDC peak intensity between 1120 and 1150 cm$^{-1}$ was displayed over the area using a color map to depict intensity variation. This peak was chosen because it showed the highest signal intensity (data not shown). The color scale was kept constant across all of the images to allow for a fair comparison between them. In contrast, little to no Raman signal was detected from cells incubated with AuNP-DTDC@SiO2-PpIX without TAT (data not shown), which is in good agreement with the TPL imaging results.

Photodynamic Therapy. The efficacy of the theranostic construct was demonstrated using live/dead cell staining after exposing nanoparticle-incubated cells to UV light. The treatment group was incubated with AuNS-DTDC@SiO$_2$—PpIX-TAT for 1 hour while the control group was incubated with AuNS-DTDC@SiO$_2$-TAT for 1 hour (particle concentration of 0.1 nM). The cells were washed 3× in PBS and then exposed to light for 30 seconds from a mercury arc lamp after passing through a DAPI filter (377/50 nm). A 40× objective was used to focus the light onto the cell sample, with a measured power density of 4.4 W cm$^2$. After treatment, cells were cultured for 4 hours in complete growth medium prior to viability staining (data not shown). Cell death due to PDT was highly evident in (data not shown). There appeared to be some cell detachment in the control group (data not shown) due to heating of the nanoparticles, but the result is not as dramatic as that seen with the PpIX-loaded particles. While not wishing to be limited to any specific mechanism, the mechanism of photo-cytotoxicity was ascribed to the $^1O_2$ generated by PpIX when excited by the broadband light within its absorption band. This $^1O_2$ can diffuse out of the porous silica matrix and travel on the order of tens of nanometers to affect cellular components. While the excitation light did heat the particles enough to cause cell detachment, very few of the cells were actually ablated (data not shown). The effect of using PpIX-loaded particles without TAT was also tested. Light exposure after a 1-hour incubation with 0.1 nM AuNS-DTDC@SiO$_2$—PpIX did not produce any observable effect (data not shown).

In summary, the use of the cell-penetrating peptide, TAT, greatly increased nanostar uptake by the cells, enhancing the efficacy of our construct. SERS imaging and photosensitization were demonstrated on BT-549 breast cancer cells. When the same conditions were used for particles that were not functionalized with TAT, little to no Raman signal could be detected from the cells and no photosensitization was observed after light exposure. The particles exhibited no cytotoxic effect under dark conditions.

REFERENCES

1. Kievit, F. M.; Zhang, M. *Adv. Mater.* (Weinheim, Ger.) 2011, 23, (36), H217-47.
2. Shi, J.; Votruba, A. R.; Farokhzad, O. C.; Langer, R. *Nano Lett.* 2010, 10, (9), 3223-3230.
3. Farrell, D.; Alper, J.; Ptak, K.; Panaro, N. J.; Grodzinski, P.; Barker, A. D. *ACS Nano* 2010, 4, (2), 589-594.
4. Chadwick, S.; Kriegel, C.; Amiji, M. *Adv. Drug Delivery Rev.* 2010, 62, (4-5), 394-407.
5. Riehemann, K.; Schneider, S. W.; Luger, T. A.; Godin, B.; Ferrari, M.; Fuchs, H. *Angew. Chem., Int. Ed. Engl.* 2009, 48, (5), 872-897.
6. Wang, X.; Yang, L.; Chen, Z. G.; Shin, D. M. *CA Cancer J Clin* 2008, 58, (2), 97-110.
7. Nie, S.; Xing, Y.; Kim, G. J.; Simons, J. W. *Annu. Rev. Biomed. Eng.* 2007, 9, 257-288.
8. Hahn, M. A.; Singh, A. K.; Sharma, P.; Brown, S. C.; Moudgil, B. M. *Anal. Bioanal. Chem.* 2011, 399, (1), 3-27.
9. Ghosh, P.; Han, G.; De, M.; Kim, C. K.; Rotello, V. M. *Adv. Drug Delivery Rev.* 2008, 60, (11), 1307-1315.
10. Huang, L.; Liu, Y. *Annu. Rev. Biomed. Eng.* 2011, 13, (1), 507-530.
11. Juzenas, P.; Chen, W.; Sun, Y.-P.; Neto Coelho, M. A.; Generalov, R.; Generalova, N.; Christensen, I. L. *Adv. Drug Delivery Rev.* 2008, 60, (15), 1600-1614.
12. Kennedy, L. C.; Bickford, L. R.; Lewinski, N. A.; Coughlin, A. J.; Hu, Y.; Day, E. S.; West, J. L.; Drezek, R. A. *Small* 2011, 7, (2), 169-183.
13. Ruoslahti, E.; Bhatia, S. N.; Sailor, M. J. *J. Cell Biol.* 2010, 188, (6), 759-768.
14. Peer, D.; Karp, J. M.; Hong, S.; Farokhzad, O. C.; Margalit, R.; Langer, R. *Nat. Nanotechnol.* 2007, 2, (12), 751-760.
15. Hu, M.; Chen, J.; Li, Z.-Y.; Au, L.; Hartland, G. V.; Li, X.; Marquez, M.; Xia, Y. *Chem. Soc. Rev.* 2006, 35, (11), 1084-1094.
16. Boisselier, E.; Astruc, D. *Chem. Soc. Rev.* 2009, 38, (6), 1759-1782.
17. Weissleder, R. *Nat. Biotechnol.* 2001, 19, (4), 316-317.
18. Guerrero-Martínez, A.; Barbosa, S.; Pastoriza-Santos, I.; Liz-Marzán, L. M. *Curr. Opin. Colloid Interface Sci.* 2011, 16, (2), 118-127.
19. Yuan, H.; Khoury, C. G.; (co-first author); Hwang, H.; Wilson, C. M.; Grant, G. A.; Vo-Dinh, T. *Nanotechnology* 2012, 23, (7), 075102.
20. Yuan, H.; Khoury, C. G.; Wilson, C. M.; Grant, G. A.; Bennett, A. J.; Vo-Dinh, T. *Nanomedicine: NBM* 2012.
21. Austin, L. A.; Kang, B.; Yen, C.-W.; El-Sayed, M. A. *J. Am. Chem. Soc.* 2011, 133, (44), 17594-17597.
22. Tkachenko, A. G.; Xie, H.; Liu, Y.; Coleman, D.; Ryan, J.; Glomm, W. R.; Shipton, M. K.; Franzen, S.; Feldheim. D. L. *Bioconjugate Chem.* 2004, 15, (3), 482-490.
23. Tong, L.; Wei, Q.; Wei, A.; Cheng, J.-X. *Photochem. Photobiol.* 2009, 85, (1), 21-32.
24. Hutter, E.; Maysinger, D. *Microsc. Res. Tech.* 2010, 74, (7), 592-604.
25. Van de Brock, B.; Devoogdt, N.; D'Hollander, A.; Gijs, H.-L.; Jans, K.; Lagae, L.; Muyldermans, S.; Maes, G.; Borghs, G. *ACS Nano* 2011, 5, (6), 4319-4328.
26. ANSI, *American National Standard for safe use of lasers.* Laser Institute of America: Orlando, Fla., 2000.
27. Huang, X.; Kang, B.; Qian, W.; Mackey, M. A.; Chen, P. C.; Oyelere, A. K.; El-Sayed, I. H.; El-Sayed, M. A. *J. Biomed. Opt.* 2010, 15, (5), 058002.
28. Au, L.; Zheng, D.; Zhou, F.; Li, Z.-Y.; Li, X.; Xia, Y. *ACS Nano* 2008, 2, (8), 1645-1652.
29. Kim, J.; Park, S.; Lee, J. E.; Jin, S. M.; Lee, J. H.; Lee, I. S.; Yang, I.; Kim, J.-S.; Kim, S. K.; Cho, M.-H.; Hyeon, T. *Angew. Chem., Int. Ed. Engl.* 2006, 45, (46), 7754-7758.
30. Patel, L.; Zaro, J.; Shen, W.-C. *Pharm. Res.* 2007, 24, 1977-1992.
31. Khalil, I. A.; Kogure, K.; Akita, H.; Harashima, H. *Pharmacol. Rev.* 2006, 58, (1), 32-45.
32. Lévy, R.; Shaheen, U.; Cesbron, Y. *Nano Rev.* 2010, 1, 4889.
33. Lundqvist, M.; Stigler, J.; Elia, G.; Lynch, I.; Cedervall, T.; Dawson, K. A. *Proc. Natl. Acad. Sci. U.S.A* 2008, 105, (38), 14265-14270.
34. Bartczak, D.; Musicals, O. L.; Nitti, S.; Sanchez-Elsner, T.; Millar, T. M.; Kanaras, A. G. *Small* 2011.
35. Torchilin, V. P. *Adv. Drug Delivery Rev.* 2008, 60, (4-5), 548-558.
36. Wei, Y.; Jana, N. R.; Tan, S. J.; Ying, J. Y. *Bioconjugate Chem.* 2009, 20, (9), 1752-1758.
37. Zhao, M.; Kircher, M. F.; Josephson, L.; Weissleder, R. *Bioconjugate Chem.* 2002, 13, (4), 840-844.
38. Rao, K. S.; Reddy, M. K.; Horning, J. L.; Labhasetwar, V. *Biomaterials* 2008, 29, (33), 4429-4438.
39. Tian, X.-h.; Wei, F.; Wang, T.-x.; Wang, D.; Wang, J.; Lin, X.-n.; Wang, P.; Ren, L. *Mater. Lett.* 2012, 68, 94-96.
40. Wadia, J. S.; Stan, R. V.; Dowdy, S. F. *Nat. Med.* 2004, 10, (3), 310-315.
41. Ruan, G.; Agrawal, A.; Marcus, A. I.; Nie, S. *J. Am. Chem. Soc.* 2007, 129, (47), 14759-14766.
42. Pallaoro, A.; Braun, G. B.; Moskovits, M. *Proc. Natl. Acad. Sci. U.S.A* 2011, 108, (40), 16559-16564.
43. Gregas, M. K.; Scaffidi, J.; Lauly, B.; Vo-Dinh, T. *Appl. Spectrosc.* 2010, 64, (8), 858-866.
44. Lewin, M.; Carlesso, N.; Tung, C. H.; Tang, X. W.; Cory, D.; Scadden, D. T.; Weissleder, R. *Nat. Biotechnol.* 2000, 18, (4), 410-414.
45. Krpetic, Z.; Saleemi, S.; Prior, I. A.; See, V.; Qureshi, R.; Brust, M. *ACS Nano* 2011, 5, (6), 5195-5201.
46. Berry, C. C.; de la Fuente, J. M.; Mullin, M.; Chu, S. W. L.; Curtis, A. S. G. *IEEE Trans. Nanobioscience* 2007, 6, (4), 262-269.
47. Dun, N. J.; Weisspfennig, C. T.; Holfeld, B. A.; Ben-Yakar, A. *J. Biomed. Opt.* 2011, 16, (2), 026008.
48. Pan, L.; He, Q.; Liu, J.; Chen, Y.; Ma, M.; Zhang, L.; Shi, J. *J. Am. Chem. Soc.* 2012, 120320133341008.
49. Panté, N.; Kann, M. *Mol. Biol. Cell* 2002, 13, (2), 425-434.
50. Mishra, A.; Lai, G. H.; Schmidt, N. W.; Sun, V. Z.; Rodriguez, A. R.; Tong, R.; Tang, L.; Cheng, J.; Deming, T. J.; Kamei, D. T.; Wong, G. C. L. *Proc. Natl. Acad. Sci. U.S.A* 2011, 108, (41), 16883-16888.
51. Zhang, L. W.; Monteiro-Riviere, N. A. *Toxicol. Sci.* 2009, 110, (1), 138-155.

52. Iversen, T.-G.; Skotland, T.; Sandvig, K. *Nano Today* 2011, 6, (2), 176-185.
53. Chen S, Wang Z L. Ballato J, Foulger S H, Carroll D L. *J Am Chem Soc.* 2003 Dec. 31; 125(52):16186-7.
54. Hao F, Nehl C L, Hafner J H, Nordlander P. *Nano Lett.* 2007 March; 7(3):729-32.
55. Senthil Kumar P. Pastoriza-Santos I, Rodriguez-González B, Garcia de Abajo F J, Liz-Marzán L M. *Nanotechnology.* 2008; 19(1):015606-12.
56. Steel, A. B.; Herne, T. M.; Tarlov, M. J. Anal. Chem. 1998, 70, 4670-7.
57. Herne, T. M.; Tarlov, M. J. J. Am. Chem. Soc. 1997, 119, 8916-20.
58. Burges, J. D.; Hawkridge, F. M. Langmuir 1997, 13, 3781-6.
59. Boncheva, M.; Scheibler, L.; Lincoln, P.; Vogel, H.; Akerman, B. Langmuir 1999, 15, 4317-20.
60. Hermanson G T. *Bioconjugate techniques.* Academic Press; 2008.
61. Potyrailo R A, Conrad R C, Ellington A D, Hieftje G M. *Anal Chem. American Chemical Society;* 1998 August; 70(16): 3419-25.
62. Hainfeld et al., The British Journal of radiology, 79, 248, 2006.
63. James F Hainfeld, Daniel N Slatkin and Henry M Smilowitz, The use of gold nanoparticles to enhance radiotherapy in mice, Phys. Med. Biol. 49, 2004.
64. Sang Hyun Cho, Estimation of tumour dose enhancement due to gold nanoparticles during typical radiation treatments: a preliminary Monte Carlo study, Phys. Med. Biol. 50, 2005.
65. Minelli, C.; Lowe, S. B.; Stevens, M. M., Engineering Nanocomposite Materials for Cancer Therapy, *Small* 2010, 6, (21), 2336-2357.
66. Janib, S. M.; Moses, A. S.; MacKay, J. A. Imaging and drug delivery using theranostic nanoparticles, *Adv. Drug Deliver. Rev.* 2010, 62, (11), 1052-1063.
67. Lammers, T.; Kiessling, F.; Hennink, W. E.; Storm, G., Nanotheranostics and Image-Guided Drug Delivery: Current Concepts and Future Directions, *Mol. Pharm.* 2010, 7, (6), 1899-1912.
68. Xie, J.; Lee, S.; Chen, X., Nanoparticle-based theranostic agents, *Adv. Drug Deliver. Rev.* 2010, 62, (11), 1064-1079.
69. Mura, S.; Couvreur, P., Nanotheranostics for personalized medicine, *Adv Drug Deliv Rev* 2012, 64, (13), 1394-416.
70. Vo-Dinh, T.; Hiromoto, M. Y. K.; Begun, G. M.; Moody, R. L., Surface-enhanced Raman spectrometry for trace organic analysis, Anal. Chem. 1984, 56, (9), 1667-1670.
71. Vo-Dinh, T.; Meier, M.; Wokaun, A., Surface-enhanced Raman spectrometry with silver particles on stochastic-post substrates, Anal. Chim. Acta. 1986, 181, (0), 139-148.
72. Vo-Dinh, T., Surface-enhanced Raman spectroscopy using metallic nanostructures. Trends Analyt. Chem, 1998, 17, (8-9), 557-582.
73. Vo-Dinh, T.; Dhawan, A.; Norton, S. J.; Khoury, C. G.; Wang, H.-N.; Misra, V.; Gerhold, M. D., Plasmonic Nanoparticles and Nanowires: Design, Fabrication and Application in Sensing†, J. Phys. Chem. C 2010, 114, (16), 7480-7488.
74. Fales, A. M.; Yuan, H.; Vo-Dinh, T. Silica-Coated Gold Nanostars for Combined Surface-Enhanced Raman Scattering (SERS) Detection and Singlet-Oxygen Generation: A Potential Nanoplatform for Theranostics. Langmuir 2011, 27, (19), 12186-12190.
75. Yuan, H.; Fales, A. M.; Vo-Dinh, T. TAT Peptide-Functionalized Gold Nanostars: Enhanced Intracellular Delivery and Efficient NIR Photothermal Therapy Using Ultralow Irradiance. J. Am. Chem. Soc. 2012, 134, (28), 11358-11361.
76. Yuan, H.; Khoury, C. G.; Wilson, C. M.; Grant, G. A.; Bennett, A. J.; Vo-Dinh, T. In vivo particle tracking and photothermal ablation using plasmon-resonant gold nanostars. Nanomedicine 2012, 8, (8), 1355-63.
77. Mint, Š.; Rao, S.; Marro, M.; Miškovský, P.; Petrov, D. Monitoring of local pH in photodynamic therapy-treated live cancer cells using surface-enhanced Raman scattering probes. J. Raman Spectrosc. 2011, 42, (6), 1215-1221.
78. Kircher, M. F.; de la Zerda, A.; Jokerst, J. V.; Zavaleta, C. L.; Kempen, P. J.; Mittra, E.; Piller, K.; Huang, R.; Campos, C.; Habte, F.; Sinclair, R.; Brennan, C. W.; Mellinghoff, I. K.; Holland, E. C.; Gambhir, S. S. A brain tumor molecular imaging strategy using a new triple-modality MRI-photoacoustic-Raman nanoparticle. Nat Med 2012, 18, (5), 829-834.
79. Alvarez-Puebla, R. A.; Liz-Marzán, L. M. SERS-Based Diagnosis and Biodetection. Small 2010, 6, (5), 604-610.
80. Kneipp, J.; Kneipp, H.; Wittig, B.; Kneipp, K. Following the Dynamics of pH in Endosomes of Live Cells with SERS Nanosensorst†. J. Phys. Chem. C 2010, 114, (16), 7421-7426.
81. Kneipp, J.; Kneipp, H.; Rice, W. L.; Kneipp, K. Optical Probes for Biological Applications Based on Surface-Enhanced Raman Scattering from Indocyanine Green on Gold Nanoparticles. Anal. Chem. 2005, 77, (8), 2381-2385.
82. Kneipp, J.; Kneipp, H.; Rajadurai, A.; Redmond, R. W.; Kneipp, K. Optical probing and imaging of live cells using SERS labels. J. Raman Spectrosc. 2009, 40, (1), 1-5.
83. Qian, X. M.; Nie, S. M. Single-molecule and single-nanoparticle SERS: from fundamental mechanisms to biomedical applications. Chem. Soc. Rev. 2008, 37, (5), 912-920.
84. Faulds, K.; Smith, W. E.; Graham, D. Evaluation of Surface-Enhanced Resonance Raman Scattering for Quantitative DNA Analysis. Anal. Chem. 2003, 76, (2), 412-417.
85. Rodriguez-Lorenzo, L.; Krpetic, Z.; Barbosa, S.; Alvarez-Puebla, R. A.; Liz-Marzan, L. M.; Prior, I. A.; Brust, M. Intracellular mapping with SERS-encoded gold nanostars. Integr. Biol. 2011, 3, (9), 922-926.
86. Küstner, B.; Winer, M.; Schütz, M.; Schöppler, F.; Marx, A.; Ströbel, P.; Adam, P.; Schmuck, C.; Schlücker, S. SERS Labels for Red Laser Excitation: Silica-Encapsulated SAMs on Tunable Gold/Silver Nanoshells. Angew. Chem. Int. Edit. 2009, 48, (11), 1950-1953.
87. Cao, Y. C.; Jin, R.; Nam, J.-M.; Thaxton, C. S.; Mirkin, C. A. Raman Dye-Labeled Nanoparticle Probes for Proteins. J. Am. Chem. Soc. 2003, 125, (48), 14676-14677.
88. Wang, G.; Park, H.-Y.; Lipert, R. J.; Porter, M. D. Mixed Monolayers on Gold Nanoparticle Labels for Multiplexed Surface-Enhanced Raman Scattering Based Immunoassays. Anal. Chem. 2009, 81, (23), 9643-9650.
89. Gregas, M. K.; Yan, F.; Scaffidi, J.; Wang, H.-N.; Vo-Dinh, T. Characterization of nanoprobe uptake in single cells: spatial and temporal tracking via SERS labeling and modulation of surface charge. Nanomedicine: NBM 2011, 7, (1), 115-122.
90. Gregas, M. K.; Scaffidi, J. P.; Lauly, B.; Vo-Dinh, T. Surface-Enhanced Raman Scattering Detection and Tracking of Nanoprobes: Enhanced Uptake and Nuclear Targeting in Single Cells. Appl. Spectrosc. 2010, 64, (8), 858-866.
91. Zavaleta, C. L.; Smith, B. R.; Walton, I.; Doering, W.; Davis, G.; Shojaei, B.; Natan, M. J.; Gambhir, S. S. Multiplexed imaging of surface enhanced Raman scattering nanotags in living mice using noninvasive Raman spectroscopy. Proc. Natl. Acad. Sci. USA 2009, 106, (32), 13511-13516.
92. Keren, S.; Zavaleta, C.; Cheng, Z.; de la Zerda, A.; Gheysens, O.; Gambhir, S. S. Noninvasive molecular imaging of small living subjects using Raman spectroscopy. Proc. Natl. Acad. Sci. USA 2008, 105, (15), 5844-5849.
93. Kim, J.-H.; Kim, J.-S.; Choi, H.; Lee, S.-M.; Jun, B.-H.; Yu, K.-N.; Kuk, E.; Kim, Y.-K.; Jeong, D. H.; Cho, M.-H.; Lee, Y.-S. Nanoparticle Probes with Surface Enhanced Raman Spectroscopic Tags for Cellular Cancer Targeting. Anal. Chem. 2006, 78, (19), 6967-6973.
94. Küstner, B.; Gellner, M.; Schütz, M.; Schöppler, F.; Marx, A.; Strübel, P.; Adam, P.; Schmuck, C.; Schlücker, S. SERS-Marker für die Anregung mit rotem Laserlicht: Glasverkapselte SAMs auf Gold/Silber-Nanoschalen. Angew. Chem. 2009, 121, (11), 1984-1987.
95. Lam, M.; Oleinick, N. L.; Nieminen, A.-L. Photodynamic Therapy-induced Apoptosis in Epidermoid Carcinoma Cells. J. Biol. Chem. 2001, 276, (50), 47379-47386.
96. Tang, W.; Xu, H.; Kopelman, R.; Philbert, M. A. Photodynamic Characterization and In Vitro Application of Methylene Blue-containing Nanoparticle Platforms. Photochem. Photobiol. 2005, 81, (2), 242-249.
97. Rossi, L. M.; Silva, P. R.; Vono, L. L. R.; Fernandes, A. U.; Tada, D. B.; Baptista, M. c. S. Protoporphyrin IX Nanoparticle Carrier: Preparation, Optical Properties, and Singlet Oxygen Generation. Langmuir 2008, 24, (21), 12534-12538.
98. Lee, S. J.; Koo, H.; Lee, D.-E.; Min, S.; Lee, S.; Chen, X.; Choi, Y.; Leary, J. F.; Park, K.; Jeong, S. Y.; Kwon, I. C.; Kim, K.; Choi, K. Tumor-homing photosensitizer-conjugated glycol chitosan nanoparticles for synchronous photodynamic imaging and therapy based on cellular on/off system. Biomaterials 2011, 32, (16), 4021-4029.
99. Bechet, D.; Couleaud, P.; Frochot, C.; Viriot, M.-L.; Guillemin, F.; Barberi-Heyob, M. Nanoparticles as vehicles for delivery of photodynamic therapy agents. Trends Biotechnol. 2008, 26, (11), 612-621.
100. Roy, I.; Ohulchanskyy, T. Y.; Pudavar, H. E.; Bergey, E. J.; Oseroff, A. R.; Morgan, J.; Dougherty, T. J.; Prasad, P. N. Ceramic-Based Nanoparticles Entrapping Water-Insoluble Photosensitizing Anticancer Drugs: A Novel Drug-Carrier System for Photodynamic Therapy. J. Am. Chem. Soc. 2003, 125, (26), 7860-7865.
101. Ohulchanskyy, T. Y.; Roy, I.; Goswami, L. N.; Chen, Y.; Bergey, E. J.; Pandey, R. K.; Oseroff, A. R.; Prasad, P. N. Organically Modified Silica Nanoparticles with Covalently Incorporated Photosensitizer for Photodynamic Therapy of Cancer. Nano Lett. 2007, 7, (9), 2835-2842.
102. Kim, S.; Ohulchanskyy, T. Y.; Pudavar, H. E.; Pandey, R. K.; Prasad, P. N. Organically Modified Silica Nanoparticles Co-encapsulating Photosensitizing Drug and Aggregation-Enhanced Two-Photon Absorbing Fluorescent Dye Aggregates for Two-Photon Photodynamic Therapy. J. Am. Chem. Soc. 2007, 129, (9), 2669-2675.
103. Yan, F.; Kopelman, R. The Embedding of Meta-tetra (Hydroxyphenyl)-Chlorin into Silica Nanoparticle Platforms for Photodynamic Therapy and Their Singlet Oxygen Production and pH-dependent Optical Properties. Photochem. Photobiol. 2003, 78, (6), 587-591.
104. Lu, J.; Liong, M.; Zink, J. I.; Tamanoi, F. Mesoporous Silica Nanoparticles as a Delivery System for Hydrophobic Anticancer Drugs. Small 2007, 3, (8), 1341-1346.
105. Yuan, H.; Fales, A. M.; Khoury, C. G.; Liu, J.; Vo-Dinh, T., J. Raman Spectrosc. 2012.
106. Fernández-López, C.; Mateo-Mateo, C.; Álvarez-Puebla, R. n. A.; Pérez-Juste, J.; Pastoriza-Santos, I.; Liz-Marzán, L. M. Highly Controlled Silica Coating of PEG-Capped Metal Nanoparticles and Preparation of SERS-Encoded Particles†. Langmuir 2009, 25, (24), 13894-13899.

Any patents or publications mentioned in this specification are indicative of the levels of those skilled in the art to which the present disclosure pertains. These patents and publications are herein incorporated by reference in their entirety to the same extent as if each individual publication was specifically and individually indicated to be incorporated by reference.

One skilled in the art will readily appreciate that the present disclosure is well adapted to carry out the objects and obtain the ends and advantages mentioned, as well as those inherent therein. The present examples along with the methods described herein are presently representative of preferred embodiments, are exemplary, and are not intended as limitations on the scope of the invention. Changes therein and other uses will occur to those skilled in the art which are encompassed within the spirit of the present disclosure as defined by the scope of the claims.

We claim:

1. A Trans-Activator of Transcription (TAT)-functionalized plasmonics-active gold nanostar having a size ranging from about 30 nm to about 80 nm, wherein a plasmon peak of the nanostar ranges from about 600 nm to about 1000 nm, wherein the nanostar comprises a layer surrounding the nanostar, a Human immunodeficiency virus type 1 (HIV-1) TAT peptide, an additional bioreceptor, and one or more of an optical or a non-optical label, a photosensitizer, or a photoactivator, and wherein the additional bioreceptor is one or more of a cell penetrating peptide (CPP), a Multiple Antigenic Peptide (MAP), angiopep2 peptide, transferrin, a Human Epidermal Growth Factor Receptor 2 (HER2) antibody, a Trastuzumab antibody, anti-epidermal growth factor receptor (EGFR) antibody, a nucleic acid, a DNA, a cell surface receptor, or an aptamer, and wherein the layer surrounding the nanostar consists of one or more of silica, poly(N-isopropylacrylamide) or polyethylene glycol.

2. The gold nanostar of claim 1, wherein the gold nano star comprises the optical or non-optical label, the photosensitizer, or the photoactivator, and each of the optical or non-optical label, the photosensitizer, and the photoactivator absorb electromagnetic radiation emitted by the gold nanostar when the gold nanostar is excited by a single-photon or multi-photon excitation.

3. The gold nanostar of claim 1, wherein the gold nanostar comprises the optical label, and the optical label comprises one or more of a fluorescence label, a Fluorescein, a Rhodamine, a phosphorescence label, a Raman label, a 3,3'-Diethylthiadicarbocyanine iodide (DTDC) label, a photoacoustic label, an optical coherence tomography (OCT) label, and an absorbance label.

4. The gold nanostar of claim 1, wherein the gold nanostar comprises the non-optical label, and the non-optical label comprises one or more of a magnetic resonance imaging (MRI) label, a 1,4,7,10-Tetraazacy-clododecane-1,4,7,10-tetraacetic acid (DOTA) conjugated to a contrast agent label, a positron emission tomography (PET) label, a DOTA conjugated to a PET contrast agent label, and an ultrasound label.

5. The gold nanostar of claim 1, wherein the additional bioreceptor is one or more of a cell penetrating peptide (CPP), a Multiple Antigenic Peptide (MAP), angiopep2 peptide, transferrin, a nucleic acid, a DNA, a cell surface receptor, and an aptamer.

6. The gold nanostar of claim 1, wherein the one or more of the optical or non-optical label, the photosensitizer, the photoactivator, or the additional bioreceptor are adsorbed or covalently attached to the gold nanostar.

7. The gold nanostar of claim 6, further comprising a drug embedded in an additional layer surrounding the gold nanostar such that the drug is released or activated via one or more of passive diffusion release, photochemically triggered release, thermal triggered release, pH triggered release, photochemical activation, and thermal activation.

8. The gold nanostar of claim 7, wherein the drug comprises one or more of a drug that is beneficial to a cell, a drug that is detrimental to a cell, and a small interference RNA (siRNA) designed to bind to mRNA in order to trigger or prevent gene expression.

9. The gold nanostar of claim 1, further comprising a coating comprising silica.

10. A cysteine-terminated Trans-Activator of Transcription (cTAT)-functionalized, plasmonics-active gold nanostar having a size ranging from about 30 nm to about 80 nm, wherein a plasmon peak of the nano star ranges from about 600 nm to about 1000 nm, wherein the nanostar comprises a cysteine-terminated human immunodeficiency virus type 1 (HIV-1) Trans-Activator of Transcription (cTAT) peptide, and one or more of an additional bioreceptor, an optical or a non-optical label, a photosensitizer, or a photoactivator, and wherein the additional bioreceptor, if present, is one or more of a cell penetrating peptide (CPP), a Multiple Antigenic Peptide (MAP), angiopep2 peptide, transferrin, a Human Epidermal Growth Factor Receptor 2 (HER2) antibody, a Trastuzumab antibody, anti-epidermal growth factor receptor (EGFR) antibody, a nucleic acid, a DNA, a cell surface receptor, or an aptamer.

11. The gold nanostar of claim 10, further comprising a drug embedded in a layer surrounding the gold nanostar such that the drug is released or activated via one or more of passive diffusion release, photochemically triggered release, thermal triggered release, pH triggered release, photochemical activation, and thermal activation.

12. The gold nanostar of claim 11, wherein the drug comprises one or more of a drug that is beneficial to a cell, a drug that is detrimental to a cell, and a small interference RNA (siRNA) designed to bind to mRNA in order to trigger or prevent gene expression.

* * * * *